US008008452B2

(12) United States Patent
Bichsel et al.

(10) Patent No.: US 8,008,452 B2
(45) Date of Patent: Aug. 30, 2011

(54) PHOSPHORYLATED NDR KINASE

(75) Inventors: Samuel Joseph Bichsel, Basel (CH); Brian Arthur Hemmings, Bettingen (CH); Mario Reinhard Stegert, Grenzach (DE); Rastislav Tamaskovic, Rheinfelden (CH)

(73) Assignee: Novartis Forschungsstiftung, Zweigniederlassung Friedrich Miescher Institute for Biomedical Research, Basel (CH)

( * ) Notice: Subject to any disclaimer, the term of this patent is extended or adjusted under 35 U.S.C. 154(b) by 286 days.

(21) Appl. No.: 10/535,920

(22) PCT Filed: Nov. 25, 2003

(86) PCT No.: PCT/EP03/13251
§ 371 (c)(1),
(2), (4) Date: Dec. 21, 2005

(87) PCT Pub. No.: WO2004/048576
PCT Pub. Date: Jun. 10, 2004

(65) Prior Publication Data
US 2006/0172374 A1   Aug. 3, 2006

(30) Foreign Application Priority Data
Nov. 26, 2002   (GB) .................................. 0227562.6

(51) Int. Cl.
C07K 16/40   (2006.01)
C07K 16/00   (2006.01)
(52) U.S. Cl. ............. 530/388.26; 530/387.1; 530/387.3; 530/388.1
(58) Field of Classification Search .................. None
See application file for complete search history.

(56) References Cited

U.S. PATENT DOCUMENTS
5,981,205 A * 11/1999 Hemmings et al. ............ 435/15

FOREIGN PATENT DOCUMENTS
EP          1097989        5/2001
WO          WO 96/19579    6/1996
WO          WO 97/18303    5/1997

OTHER PUBLICATIONS

Millward et al. (1995) Proc. Natl. Acad. Sci. USA, vol. 92, pp. 5022-5026.*
Lederman et al. Molecular Immunology 28: 1171-1181, 1991.*
Li et al. PNAS 77: 3211-3214, 1980.*
Attwood Science 2000; 290:471-473.*
Skolnick et al. Trends in Biotech. 2000; 18(1):34-39.*
Campbell (Monoclonal Antibody Technology, 1984, Chapter 1, pp. 1-32).*
Strausberg, et al., "Serine/threonine kinase 38 like", Database Uniprot Online, EMBL (Jun. 1, 2002).
Strausberg, et al., Homo sapiens serine/threonine kinase 38 like, mRNA (cDNA clone MGC: 33176 Image: 4823429), PNAS, vol. 99, pp. 16899-16903 (Apr. 27, 2002).
Millward, et al., "Calcium regulation of Ndr protein kinase mediated by S100 calcium-binding proteins", Embo J., vol. 17, pp. 5913-5922 (1998).
Tamaskovic, et al., "Mechanism of Ca2+-mediated regulation of Ndr protein kinase through autophorphorylation and phorphorylation by an upstream kinase", J. of Bio. Chem., vol. 278, pp. 6710-6718 (Feb. 28, 2003).
Tamaskovic, et al., "Ndr family of AGC kinases—essential regulators of the cell cycle and morphogenesis", FEBS Letters, vol. 546, No. 1, pp. 73-80 (Jul. 3, 2003).
Akimoto, K. et al., Atypical protein kinase C binds and regulates p70 S6 kinase, Biochem.J. 335, 417-424, (1998).
Alessi, D.R. et al., Mechanism of activation of protein kinase B by insulin and IGF-1, EMBO J. 15, 6541-6551, (1996).
Balendran, A. et al., Further evidence that 3-phosphoinositide-dependent protein kinase-1 (PDK1) is required for the stability and phosphorylation of protein kinase C (PKC) isoforms, FEBS Lett. 484, 217-223, (2000).
Behn-Krappa, A. et al., The hydrophobic phosphorylation motif of conventional protein kinase C is regulated by autophosphorylation, Curr. Biol. 9, 728-737, (1999).
Belham, C., et al., Intracellular signaling: PDK1—a kinase at the hub of things, Curr. Biol. 9, R93-R96, (1999).
Berridge, M.J. et al., The versatility and universality of calcium signaling, Nat. Rev. Mol. Cell Biol. 1, 11-21, (2000).
Carr, S.A. et al., Selective detection and sequencing of phosphopeptides at the femtomole level by mass spectrometry, Anal. Biochem. 239, 180-192, (1996).
Delcommenne, M. et al., Phosphoinositide-3-OH-kinase-dependent regulation of glycogen synthase kinase 3 and protein kinase B / AKT by the integrin-linked kinase, Proc. Natl. Acad. Sci. U.S.A. 95, 11211-11216, (1998).
Durrenberger, F. et al., The ukc1 gene encodes a protein kinase involved in morphogenesis, pathogenicity and pigment formation in Ustilago maydis, Mol. Gen. Genet. 261, 281-289, (1999) (Abstract Only).
Evan, G. et al., Isolation of monoclonal antibodies specific for human c-myc proto-oncogene product, Mol. Cell Biol. 5, 3610-3616, (1985).
Fujisawa, H., Regulation of the activities of multifunctional $Ca^{2+}$/Calmodulin-dependent protein kinase, J.Biochem. 129, 193-199, (2001), Tokyo.
Geng, W. et al., the *tricornered* gene, which is required for the integrity of epidermal cell extensions, encodes the drosophila nuclear DBF2-related kinase, Genetics 156, 1817-1828, (2000).
Haby, C. et al., Inhibition of serine/threonine protein phosphatases promotes opening of voltage-activated L-type $Ca^{2+}$channels in insulin-secreting cells, Biochem.J. 298, 341-346, (1994).
Hanks et al., The protein kinase family: conserved features and deduced phylogeny of the catalytic domains, Methods in Enzymology 200, 38-62, (1991).
Hanks, S.K. et al., Science 241, 42-52, (1988).
Heierhorst, J. et al., Ca2+/S100 regulation of giant protein kinases, Nature 380, 636-639, (1996) (Abstract Only).

(Continued)

Primary Examiner — Sharon Wen
(74) Attorney, Agent, or Firm — Hoxie & Associates LLC

(57) ABSTRACT

The present invention relates to the phosphorylated form of nuclear serine/threonine protein kinase, designated nuclear, Dbf2-related kinase (Ndr), and provides assays and materials for identifying modulators thereof. The invention relates to the fields of molecular biology, chemistry, pharmacology, and screening technology.

2 Claims, No Drawings

OTHER PUBLICATIONS

Hepworth, T.J. et al., Okadiac acid induces the release of Ca2+ from intracellular stores in ECV304 endothelial cells, Cell Calcium 21, 461-467, (1997) (Abstract Only).

Hill, M.M. et al., Identification of a plasma membrane raft-associated PKB Ser 473 kinase activity that is distinct from ILK and PDK1, Curr.Biol. 12, 1251, (2002).

Hill, M.M. et al., Insulitin-stimulated protein kinase B phosphorylation on Ser-473 is independent of its activity and occurs through a staurosphorine-insensitive kinase, J.Biol.Chem. 276, 25643-25646, (2001).

ILG, E.C. et al., Expression pattern of S100 calcium-binding proteins in human tumors, Int.J.Cancer 68, 325-332, (1996).

Jaspersen, S.L. et al., A late mitotic regulatory network controlling cyclin destruction in *saccaramyces cerevisiae*, Mol. Biol. Cell 9, 2803-2817, (1998).

Johnston, L.H. et al., The product of the *saccaromyces cerevisiae* cell cycle gene DBF2 has homology with protein kinases and is periodically expressed in the cell cycle, Mol.Cell.Bio1.10, 1358-1366, (1990).

Justice, R.W. et al., The *Drosphilia* tumor suppressor gene *warts* encodes a homolog of human myotonic dystrophy kinase and is required for the control of cell shape and proliferation, Genes & Development 9, 534-546, (1995).

Knighton, D.R. et al. Crystal structure of the catalytic subunit of cyclic adenosine momophosphate-dependent protein kinase, Science 253, 407-414, (1991).

LeGood, J.A. et al., Protein kinase C isotypes controlled by phosphoinositide 3-kinase through the protein kinase PDK1, Science 281, 2042-2045, (1998).

Leslie, N.R. et al., Phosphoinositide-regulated kinases and phosphoinositide phosphatases, Chem.Rev. 101, 2365-2380, (2001).

Lynch, D.K. et al., Integrin-linked kinase regulated phosphorylation of serine 473 of protein kinase B by an indirect mechanism, Oncogene 18, 8024-8032, (1999).

Millward, T.A. et al., Ndr protein kinase is regulated by phosphorylation on two conserved sequence motifs, J.Biol.Chem.274, 33847-33850, (1999).

Newton, A.C., Protein kinase C: structural and spatial regulation by phosphorylation, cofactors, and macromolecular interactions, Chem. Rev. 101, 2353-2364, (2001).

Parker, P.J. et al., AGC protein kinase phosphorylation and protein kinase C, Biochem.Soc.Trans. 29, 860-863, (2001).

Peterson, R.T. et al., Kinase phosphorylation: keeping it all in the family, Curr.Biol. 9, R521-R524, (1999).

Racki, W.J. et al., Cbk1p, a protein similar to the human myotonic dystrophy kinase, is essential for normal morphogenesis in *Saccaromyces cerevisiae*, EMBO J. 19, 4524-4532, (2000).

Romanelli, A. et al., p70 S6 kinase is regulated by protein kinase C and participates in a phosphoinositide 3-kinase regulated signalling complex, Mol. Cell Biol. 19, 2921-2928, (1999).

Shaw, M. et al., The activation of protein kinase B by $H_2O_2$ or heat shock is medicated by phosphoinositide 3-kinase and not by mitogen-activated protein kinase-activated protein kinase-2, Biochem. J. 336, 241-246, (1998).

Smith, D.B. et al., Single-step purification of polypeptides expressed in *Escherichia coil* as fusions with glutathione S-transferase, Elsevier B.V. (1988) (Abstract Only).

St. John, M.A.R. et al., Mice deficient of *Lats1* develop soft-tissue sarcomas, ovarian tumours and pituitary dysfunction, Nature Genetics 21, 182-186, (1999).

Tao, W. et al., Human homologue of the *Drosophila melanogaster lats* tumour suppressor modulates CDC2 activity, Nature Genetics 21, 177-181, (1999).

Taylor, C.W. et al., Pharmacological analysis of intracellular $Ca^{2+}$ signaling: problems and pitfalls, Trends Pharmacol. Sci. 19, 370-375, (1998).

Toyn J.H. et al., The Dbf2 and Dbf20 protein kinases of budding yeast are activated after the metaphase to anaphase cell cycle transition, EMBO J. 13, 1103-1113, (1994).

Treiman, M. et al., A tool coming of age: thapsigargin as an inhibitor of sarco-endoplasmic reticulum $Ca^{2+}$-ATPases, Trends Pharmacol. Sci. 19, 131-135 (1998).

Tripodis, N. et al., Construction of a high-resolution 2.5-Mb transcript map of the human 6p21.2-6p21.3 region immediately centromeric of the major histocompatibility comples, Genome Res. 10, 454-472, (2000).

Verde, F. et al., Fission yeast *orb6*, a ser/thr protein kinase related to mammalian rho kinase and myotonic dystrophy kinase, is required for the maintenance of cell polarity and coordinates cell morphygenesis with the cell cycle, Proc. Nat'l. Acad. Sci. USA 95, 7526-7531, (1998).

Williams, M.R. et al., The role of 3-phosphoinositide-dependent protein kinase 1 in activating AGC kinases defined in embryonic stem cells, Curr. Biol. 10, 439-448, (2000).

Wilm, M. et al., Analytical properties of the nanoelectrospray ion source, Anal. Chem. 68, 1-8, (1996).

Wilm, M. et al., Parent ion scans of unseparated peptide mixtures, Anal. Chem. 68, 527-533, (1996).

Xu, T. et al., Identifying tumor suppressors in genetic mosaics: the *Drosophila lats* gene encodes a putative protein kinase, Development 121, 1053-1063, (1995).

Yamasaki, R. et al., Titin-actin interaction in mouse myocardium: passive tension modulation and it regulation by calcium/S100A1, Biophys. J. 81, 2297-2313, (2001).

Yang J. et al., Molecular mechanism for the regulation of protein kinase B/Akt by hydrophobic motif phosphorylation, Mol. Cell 9, 1227-1240, (2002).

Yarden, O. et al., cot-1, a gene required for hyphal elongation in *Neurospora crassa*, encodes a protein kinase, EMBO J. 11, 2159-2166, (1992).

Yonemoto, W. et al., Autophosphorylation of the catalytic subunit of cAMP-dependent protein kinase in *Escherichiai coli*, Protein Eng. 10, 915-925, (1997).

Zallen, J.A. et al., Neuronal cell shape and neurite initiation are regulated by the Ndr kinase SAX-1, a member of the Orb6/COT-1/warts serine/threonine kinase family, Mol. Biol. Cell 11, 3177-3190, (2000).

Ziegler, W.H. et al., Rapamycin-sensitive phosphorylation of PKC on a carboxy-terminal site by an atypical PKC complex, Curr. Biol. 9, 522-529, (1999).

Millward, T.A. et al., Molecular cloning and characterization of a conserved nuclear serine (theronine) protein kinase, Proc Natl Acad Sci USA, 92,5022-26 (1995).

Koseoglu, M.M., et al., "Phosphorylation of Threonine 61 by Cyclin A/Cdk1 Triggers Degradation of Stem-Loop Binding Protein at the End of S Phase", Molecular and Cellular Biology, Jul. 2008, pp. 4469-4479, vol. 28, No. 14, American Society for Microbiology.

Wikipedia article, "Phosphorylation," http://en.wikipedia.org/wiki/Phosphorylation, (retrieved on) Jan. 20, 2010.

Maciejewski, P.M., et al., "Mutation of Serine 90 to Glutamic Acid Mimics Phosphorylation of Bovine Prolactin", The Journal of Biological Chemistry, 1995, pp. 27661-27665, vol. 270, No. 46, The American Society for Biochemistry and Molecular Biology, Inc., United States.

Alberts, B., et al., "Molecular Biology of the Cell, $3^{rd}$ Edition", 1994, pp. 86, 202-204, Garland Publishing, New York, United States.

* cited by examiner

SEQUENCE LISTING

```
<160> NUMBER OF SEQ ID NOS: 29

<210> SEQ ID NO 1
<211> LENGTH: 3018
<212> TYPE: DNA
<213> ORGANISM: Homo sapiens
<220> FEATURE:
<221> NAME/KEY: CDS
<222> LOCATION: (596)...(1990)
<223> OTHER INFORMATION: human NDR1

<400> SEQUENCE: 1
gaattccggg ccaggcatgg tagcgcatcg ctgtaatccc agctactcgg gaaactgagg      60
tgggagaatc gattgaacct ggaagtggag gttgcggtga gccaagatca tcctgtcgca     120
```

| | |
|---|---|
| ctccagcctg ggcaacaaga gcgaaactcc atctcaaaaa gaaaaaaaaa gatatatatg | 180 |
| tgtgacttac aggtacaggt aaagttgctt ctggttttct ggttgttgca tggtatttcc | 240 |
| tatgcagcca caggtcttta ttttcttact taagtgcctc caacttccca taacacaaat | 300 |
| taaggcatga tgaacatcct ctctgtgctg aacatcctgt gtatgtcact tcagaagcct | 360 |
| gtgtgacggt ttctttagtc tttataccta ggggtgggat ttctgggtca taggacagta | 420 |
| atttatattt atttcactaa gtattctctt tctctggctt ttgttacata ttacctgttt | 480 |
| gtcctccaga aaacttgcac caatttacat tcctaccaat agggtaggag agtgcacaat | 540 |
| gggtggattc taactccaaa tctaacacct cttcttttct tgtttctag cagcc atg<br>Met<br>1 | 598 |

```
gca atg aca ggc tca aca cct tgc tca tcc atg agt aac cac aca aag      646
Ala Met Thr Gly Ser Thr Pro Cys Ser Ser Met Ser Asn His Thr Lys
         5                  10                  15 gaa agg gtg aca atg acc aaa gtg aca ctg gag aat ttt tat agc aac      694
Glu Arg Val Thr Met Thr Lys Val Thr Leu Glu Asn Phe Tyr Ser Asn
            20                  25                  30 ctt atc gct caa cat gaa gaa cga gaa atg aga caa aag aag tta gaa      742
Leu Ile Ala Gln His Glu Glu Arg Glu Met Arg Gln Lys Lys Leu Glu
 35                  40                  45 aag gtg atg gaa gaa gaa ggc cta aaa gat gag gag aaa cga ctc cgg      790
Lys Val Met Glu Glu Glu Gly Leu Lys Asp Glu Glu Lys Arg Leu Arg
 50                  55                  60                  65 aga tca gca cat gct cgg aag gaa aca gag ttt ctt cgt ttg aag aga      838
Arg Ser Ala His Ala Arg Lys Glu Thr Glu Phe Leu Arg Leu Lys Arg
             70                  75                  80 aca aga ctt gga ttg gaa gat ttt gag tcc tta aaa gta ata ggc aga      886
Thr Arg Leu Gly Leu Glu Asp Phe Glu Ser Leu Lys Val Ile Gly Arg
             85                  90                  95 gga gca ttt ggt gag gta cgg ctt gtt cag aag aaa gat acg gga cat      934
Gly Ala Phe Gly Glu Val Arg Leu Val Gln Lys Lys Asp Thr Gly His
            100                 105                 110 gtg tat gca atg aaa ata ctc cgt aaa gca gat atg ctt gaa aaa gag      982
Val Tyr Ala Met Lys Ile Leu Arg Lys Ala Asp Met Leu Glu Lys Glu
        115                 120                 125 cag gtt ggc cac att cgt gcg gag cgt gac att cta gtg gag gca gac     1030
Gln Val Gly His Ile Arg Ala Glu Arg Asp Ile Leu Val Glu Ala Asp
130                 135                 140                 145 agt ttg tgg gtt gtg aaa atg ttc tat agt ttt cag gat aag cta aac     1078
Ser Leu Trp Val Val Lys Met Phe Tyr Ser Phe Gln Asp Lys Leu Asn
                150                 155                 160 ctc tac cta atc atg gag ttc ctg cct gga ggg gac atg atg acc ttg     1126
Leu Tyr Leu Ile Met Glu Phe Leu Pro Gly Gly Asp Met Met Thr Leu
            165                 170                 175 ttg atg aaa aaa gac act ctg aca gaa gag gag act cag ttt tat ata     1174
Leu Met Lys Lys Asp Thr Leu Thr Glu Glu Glu Thr Gln Phe Tyr Ile
        180                 185                 190 gca gaa aca gta tta gcc ata gac tct att cac caa ctt gga ttc atc     1222
Ala Glu Thr Val Leu Ala Ile Asp Ser Ile His Gln Leu Gly Phe Ile
    195                 200                 205 cac aga gac atc aaa cca gac aac ctt ctt ttg gac agc aag ggc cat     1270
His Arg Asp Ile Lys Pro Asp Asn Leu Leu Leu Asp Ser Lys Gly His
210                 215                 220                 225 gtg aaa ctt tct gac ttt ggt ctt tgc aca gga ctg aaa aaa gca cat     1318
Val Lys Leu Ser Asp Phe Gly Leu Cys Thr Gly Leu Lys Lys Ala His
                230                 235                 240 agg aca gaa ttt tat agg aat ctg aac cac agc ctc ccc agt gat ttc     1366
Arg Thr Glu Phe Tyr Arg Asn Leu Asn His Ser Leu Pro Ser Asp Phe
```

-continued

```
                245                 250                 255
act ttc cag aac atg aat tcc aaa agg aaa gca gaa acc tgg aaa aga      1414
Thr Phe Gln Asn Met Asn Ser Lys Arg Lys Ala Glu Thr Trp Lys Arg
            260                 265                 270 aat aga cgt cag cta gcc ttc tcc aca gta ggc act cct gac tac att      1462
Asn Arg Arg Gln Leu Ala Phe Ser Thr Val Gly Thr Pro Asp Tyr Ile
275                 280                 285 gct cct gag gtg ttc atg cag acc ggg tac aac aag ctc tgt gat tgg      1510
Ala Pro Glu Val Phe Met Gln Thr Gly Tyr Asn Lys Leu Cys Asp Trp
290                 295                 300                 305 tgg tcg ctt ggg gtg atc atg tat gag atg ctc atc ggc tac cca cct      1558
Trp Ser Leu Gly Val Ile Met Tyr Glu Met Leu Ile Gly Tyr Pro Pro
            310                 315                 320 ttc tgt tct gag acc cct caa gag aca tat aag aag gtg atg aac tgg      1606
Phe Cys Ser Glu Thr Pro Gln Glu Thr Tyr Lys Lys Val Met Asn Trp
325                 330                 335 aaa gaa act ttg act ttt cct cca gaa gtt ccc atc tct gag aaa gcc      1654
Lys Glu Thr Leu Thr Phe Pro Pro Glu Val Pro Ile Ser Glu Lys Ala
            340                 345                 350 aag gat cta att ttg agg ttc tgc tgt gaa tgg gaa cat aga att gga      1702
Lys Asp Leu Ile Leu Arg Phe Cys Cys Glu Trp Glu His Arg Ile Gly
355                 360                 365 gct cct gga gtt gag gaa ata aaa agt aac tct ttt ttt gaa ggc gtt      1750
Ala Pro Gly Val Glu Glu Ile Lys Ser Asn Ser Phe Phe Glu Gly Val
370                 375                 380                 385 gac tgg gaa cat atc aga gag aga cct gct gca ata tct att gaa atc      1798
Asp Trp Glu His Ile Arg Glu Arg Pro Ala Ala Ile Ser Ile Glu Ile
            390                 395                 400 aaa agc att gat gat acc tca aac ttc gat gag ttt cca gaa tct gat      1846
Lys Ser Ile Asp Asp Thr Ser Asn Phe Asp Glu Phe Pro Glu Ser Asp
405                 410                 415 att ctt aag cca aca gtg gcc aca agt aat cat cct gag act gac tac      1894
Ile Leu Lys Pro Thr Val Ala Thr Ser Asn His Pro Glu Thr Asp Tyr
            420                 425                 430 aag aac aaa gac tgg gtc ttc atc aat tac acg tac aag cgc ttt gag      1942
Lys Asn Lys Asp Trp Val Phe Ile Asn Tyr Thr Tyr Lys Arg Phe Glu
435                 440                 445 ggc ctg act gca agg ggg gca ata cct tcc tac atg aaa gca gca aaa      1990
Gly Leu Thr Ala Arg Gly Ala Ile Pro Ser Tyr Met Lys Ala Ala Lys
450                 455                 460                 465 tagtactctt gccacggaat cctatgtgga gcagagttct ttgtataaca tcatgctttt    2050
cctctcacac tcttgaagag cttccaagaa gttgatggaa cccaccaata tgtcatagta    2110
aagtctcctg aaatgtggta gtaagaggat tttcttccat aatgcatctg aaaaactgta    2170
aacaaagaca accatttcta ctacgtcggc cataaacagc tatcctgctt tggaagagaa    2230
gcatcatgag ccaatttgat aggtgtttta aaaataactt gagttttcct aagttcatca    2290
gaatgaaggg gaaaaacagc catcatccaa cattattgag attgtcgtgt atagtcatcg    2350
aatatcagcc agttcctgta attttgtgac acgctctctg ccaagcccac caagtatttc    2410
ctttatagct aaaagttcca tagtactaag gaaataaagc aataaagaca gtctcagcag    2470
ccaggattct ggctgaagga aatgatccgc caccctgagg gtggtgatgg tagtttctac    2530
ccatacctca gcctcaggcg agtggcttat agcctccatt catggtgcac tttatttatg    2590
gtactaagat aaagactgtc aatccattga tttatctcct cctgtccccc atctaaaata    2650
cccatgctgc ttttctgagt gttgatgggg gttaccagct tgatccactg ttgctcttag    2710
aaggcccaga aagtctttgg gcattgcaag aaatcccgaa ttatgtggaa aaccctcact    2770
```

```
ttctcttcac ggctgtacca gaaaatccct aagacagatc ttgccgtgga ctagcaatac    2830
ctgcaagtgc tgccaatggg aactcaattt attcctggga acctaacgag gagagcccag    2890
gcctaggcag gaggcctgga accctcttgg ctaaggtgct gttcctgttc ctgcaaggtc    2950
tccagaaccc ctttggaaat ggtgaaggaa ccagcccaat agaagtacag agccagctga    3010
cggaattc                                                            3018
```

<210> SEQ ID NO 2
<211> LENGTH: 465
<212> TYPE: PRT
<213> ORGANISM: Homo sapiens

<400> SEQUENCE: 2

```
Met Ala Met Thr Gly Ser Thr Pro Cys Ser Ser Met Ser Asn His Thr
  1               5                  10                  15

Lys Glu Arg Val Thr Met Thr Lys Val Thr Leu Glu Asn Phe Tyr Ser
             20                  25                  30

Asn Leu Ile Ala Gln His Glu Glu Arg Glu Met Arg Gln Lys Lys Leu
         35                  40                  45

Glu Lys Val Met Glu Glu Glu Gly Leu Lys Asp Glu Lys Arg Leu
     50                  55                  60

Arg Arg Ser Ala His Ala Arg Lys Glu Thr Glu Phe Leu Arg Leu Lys
 65                  70                  75                  80

Arg Thr Arg Leu Gly Leu Glu Asp Phe Glu Ser Leu Lys Val Ile Gly
                 85                  90                  95

Arg Gly Ala Phe Gly Glu Val Arg Leu Val Gln Lys Lys Asp Thr Gly
            100                 105                 110

His Val Tyr Ala Met Lys Ile Leu Arg Lys Ala Asp Met Leu Glu Lys
        115                 120                 125

Glu Gln Val Gly His Ile Arg Ala Glu Arg Asp Ile Leu Val Glu Ala
    130                 135                 140

Asp Ser Leu Trp Val Val Lys Met Phe Tyr Ser Phe Gln Asp Lys Leu
145                 150                 155                 160

Asn Leu Tyr Leu Ile Met Glu Phe Leu Pro Gly Gly Asp Met Met Thr
                165                 170                 175

Leu Leu Met Lys Lys Asp Thr Leu Thr Glu Glu Glu Thr Gln Phe Tyr
            180                 185                 190

Ile Ala Glu Thr Val Leu Ala Ile Asp Ser Ile His Gln Leu Gly Phe
        195                 200                 205

Ile His Arg Asp Ile Lys Pro Asp Asn Leu Leu Asp Ser Lys Gly
    210                 215                 220

His Val Lys Leu Ser Asp Phe Gly Leu Cys Thr Gly Leu Lys Lys Ala
225                 230                 235                 240

His Arg Thr Glu Phe Tyr Arg Asn Leu Asn His Ser Leu Pro Ser Asp
                245                 250                 255

Phe Thr Phe Gln Asn Met Asn Ser Lys Arg Lys Ala Glu Thr Trp Lys
            260                 265                 270

Arg Asn Arg Arg Gln Leu Ala Phe Ser Thr Val Gly Thr Pro Asp Tyr
        275                 280                 285

Ile Ala Pro Glu Val Phe Met Gln Thr Gly Tyr Asn Lys Leu Cys Asp
    290                 295                 300

Trp Trp Ser Leu Gly Val Ile Met Tyr Glu Met Leu Ile Gly Tyr Pro
305                 310                 315                 320

Pro Phe Cys Ser Glu Thr Pro Gln Glu Thr Tyr Lys Lys Val Met Asn
                325                 330                 335
```

```
Trp Lys Glu Thr Leu Thr Phe Pro Pro Glu Val Pro Ile Ser Glu Lys
            340                 345                 350

Ala Lys Asp Leu Ile Leu Arg Phe Cys Cys Glu Trp Glu His Arg Ile
            355                 360                 365

Gly Ala Pro Gly Val Glu Ile Lys Ser Asn Ser Phe Phe Glu Gly
            370                 375                 380

Val Asp Trp Glu His Ile Arg Glu Arg Pro Ala Ala Ile Ser Ile Glu
385                 390                 395                 400

Ile Lys Ser Ile Asp Asp Thr Ser Asn Phe Asp Glu Phe Pro Glu Ser
            405                 410                 415

Asp Ile Leu Lys Pro Thr Val Ala Thr Ser Asn His Pro Glu Thr Asp
            420                 425                 430

Tyr Lys Asn Lys Asp Trp Val Phe Ile Asn Tyr Thr Tyr Lys Arg Phe
            435                 440                 445

Glu Gly Leu Thr Ala Arg Gly Ala Ile Pro Ser Tyr Met Lys Ala Ala
            450                 455                 460

Lys
465

<210> SEQ ID NO 3
<211> LENGTH: 1395
<212> TYPE: DNA
<213> ORGANISM: Homo sapiens
<220> FEATURE:
<221> NAME/KEY: CDS
<222> LOCATION: (1)...(1395)
<223> OTHER INFORMATION: human NDR2

<400> SEQUENCE: 3 atg gca atg acg gca ggg act aca aca acc ttt cct atg agc aac cat    48
Met Ala Met Thr Ala Gly Thr Thr Thr Thr Phe Pro Met Ser Asn His
1               5                   10                  15 acc cgg gaa aga gtg act gta gcc aag ctc aca ttg gag aat ttt tat    96
Thr Arg Glu Arg Val Thr Val Ala Lys Leu Thr Leu Glu Asn Phe Tyr
            20                  25                  30 agc aac cta att tta cag cat gaa gag aga gaa acc agg cag aag aaa   144
Ser Asn Leu Ile Leu Gln His Glu Glu Arg Glu Thr Arg Gln Lys Lys
        35                  40                  45 tta gaa gtg gcc atg gaa gaa gaa gga tta gca gat gaa gag aaa aag   192
Leu Glu Val Ala Met Glu Glu Glu Gly Leu Ala Asp Glu Glu Lys Lys
    50                  55                  60 tta cgt cga tca caa cac gct cgc aaa gaa aca gag ttc tta cgg ctc   240
Leu Arg Arg Ser Gln His Ala Arg Lys Glu Thr Glu Phe Leu Arg Leu
65                  70                  75                  80 aaa agg acc aga ctt ggc ttg gat gac ttt gag tct ctg aaa gtt ata   288
Lys Arg Thr Arg Leu Gly Leu Asp Asp Phe Glu Ser Leu Lys Val Ile
                85                  90                  95 gga aga gga gct ttt gga gag gtg cgg ttg gtc cag aag aaa gat aca   336
Gly Arg Gly Ala Phe Gly Glu Val Arg Leu Val Gln Lys Lys Asp Thr
            100                 105                 110 ggc cat atc tat gca atg aag ata ttg aga aag tct gat atg ctt gaa   384
Gly His Ile Tyr Ala Met Lys Ile Leu Arg Lys Ser Asp Met Leu Glu
        115                 120                 125 aaa gag cag gtg gcc cat atc cga gca gaa aga gat att ttg gta gaa   432
Lys Glu Gln Val Ala His Ile Arg Ala Glu Arg Asp Ile Leu Val Glu
    130                 135                 140 gca gat ggt gcc tgg gtg gtg aag atg ttt tac agt ttt cag gat aag   480
Ala Asp Gly Ala Trp Val Val Lys Met Phe Tyr Ser Phe Gln Asp Lys
145                 150                 155                 160
```

```
agg aat ctt tat cta atc atg gaa ttt ctc cct gga ggt gac atg atg       528
Arg Asn Leu Tyr Leu Ile Met Glu Phe Leu Pro Gly Gly Asp Met Met
            165                 170                 175 aca ttg cta atg aag aaa gac acc ttg aca gaa gag gaa aca cag ttc       576
Thr Leu Leu Met Lys Lys Asp Thr Leu Thr Glu Glu Glu Thr Gln Phe
        180                 185                 190 tac att tca gag act gtt ctg gca ata gat gcg atc cac cag ttg ggt       624
Tyr Ile Ser Glu Thr Val Leu Ala Ile Asp Ala Ile His Gln Leu Gly
        195                 200                 205 ttc atc cat cgg gat att aag cca gac aac ctt tta ttg gat gcc aag       672
Phe Ile His Arg Asp Ile Lys Pro Asp Asn Leu Leu Leu Asp Ala Lys
        210                 215                 220 ggt cat gta aaa tta tct gat ttt ggt tta tgt acg gga tta aag aaa       720
Gly His Val Lys Leu Ser Asp Phe Gly Leu Cys Thr Gly Leu Lys Lys
225                 230                 235                 240 gct cac agg act gaa ttt tat aga aat ctc aca cac aac cca cca agt       768
Ala His Arg Thr Glu Phe Tyr Arg Asn Leu Thr His Asn Pro Pro Ser
                245                 250                 255 gac ttc tca ttt cag aac atg aac tca aag agg aaa gca gaa act tgg       816
Asp Phe Ser Phe Gln Asn Met Asn Ser Lys Arg Lys Ala Glu Thr Trp
            260                 265                 270 aag aag aac agg aga caa ctg gca tat tcc aca gtt ggg aca cca gat       864
Lys Lys Asn Arg Arg Gln Leu Ala Tyr Ser Thr Val Gly Thr Pro Asp
        275                 280                 285 tac att gct cca gaa gta ttc atg cag act ggt tac aac aaa ttg tgt       912
Tyr Ile Ala Pro Glu Val Phe Met Gln Thr Gly Tyr Asn Lys Leu Cys
        290                 295                 300 gac tgg tgg tct ttg gga gtg att atg tat gaa atg cta ata gga tat       960
Asp Trp Trp Ser Leu Gly Val Ile Met Tyr Glu Met Leu Ile Gly Tyr
305                 310                 315                 320 cca cct ttc tgc tct gaa aca cct caa gaa aca tac aga aaa gtg atg      1008
Pro Pro Phe Cys Ser Glu Thr Pro Gln Glu Thr Tyr Arg Lys Val Met
                325                 330                 335 aac tgg aaa gaa act ctg gta ttt cct cca gag gta cct ata tct gag      1056
Asn Trp Lys Glu Thr Leu Val Phe Pro Pro Glu Val Pro Ile Ser Glu
            340                 345                 350 aaa gcc aag gac tta att ctc aga ttt tgt att gat tct gaa aac aga      1104
Lys Ala Lys Asp Leu Ile Leu Arg Phe Cys Ile Asp Ser Glu Asn Arg
        355                 360                 365 att gga aat agt gga gta gaa gaa ata aaa ggt cat ccc ttt ttt gaa      1152
Ile Gly Asn Ser Gly Val Glu Glu Ile Lys Gly His Pro Phe Phe Glu
        370                 375                 380 ggt gtc gac tgg gag cac ata agg gaa agg cca gca gca atc cct ata      1200
Gly Val Asp Trp Glu His Ile Arg Glu Arg Pro Ala Ala Ile Pro Ile
385                 390                 395                 400 gaa atc aaa agc att gat gat act tca aat ttt gat gac ttc cct gaa      1248
Glu Ile Lys Ser Ile Asp Asp Thr Ser Asn Phe Asp Asp Phe Pro Glu
                405                 410                 415 tct gat att tta caa cca gtg cca aat acc aca gaa ccg gac tac aaa      1296
Ser Asp Ile Leu Gln Pro Val Pro Asn Thr Thr Glu Pro Asp Tyr Lys
            420                 425                 430 tcc aaa gac tgg gtt ttt ctc aat tat acc tat aaa agg ttt gaa ggg      1344
Ser Lys Asp Trp Val Phe Leu Asn Tyr Thr Tyr Lys Arg Phe Glu Gly
        435                 440                 445 ttg act caa cgt ggc tct atc ccc acc tac atg aaa gct ggg aag tta      1392
Leu Thr Gln Arg Gly Ser Ile Pro Thr Tyr Met Lys Ala Gly Lys Leu
        450                 455                 460 tga                                                                  1395
*
```

-continued

<210> SEQ ID NO 4
<211> LENGTH: 464
<212> TYPE: PRT
<213> ORGANISM: Homo sapiens

<400> SEQUENCE: 4

Met Ala Met Thr Ala Gly Thr Thr Thr Phe Pro Met Ser Asn His
1               5                   10                  15

Thr Arg Glu Arg Val Thr Val Ala Lys Leu Thr Leu Glu Asn Phe Tyr
            20                  25                  30

Ser Asn Leu Ile Leu Gln His Glu Glu Arg Glu Thr Arg Gln Lys Lys
        35                  40                  45

Leu Glu Val Ala Met Glu Glu Gly Leu Ala Asp Glu Glu Lys Lys
    50                  55                  60

Leu Arg Arg Ser Gln His Ala Arg Lys Glu Thr Glu Phe Leu Arg Leu
65                  70                  75                  80

Lys Arg Thr Arg Leu Gly Leu Asp Asp Phe Glu Ser Leu Lys Val Ile
                85                  90                  95

Gly Arg Gly Ala Phe Gly Glu Val Arg Leu Val Gln Lys Lys Asp Thr
            100                 105                 110

Gly His Ile Tyr Ala Met Lys Ile Leu Arg Lys Ser Asp Met Leu Glu
        115                 120                 125

Lys Glu Gln Val Ala His Ile Arg Ala Glu Arg Asp Ile Leu Val Glu
    130                 135                 140

Ala Asp Gly Ala Trp Val Val Lys Met Phe Tyr Ser Phe Gln Asp Lys
145                 150                 155                 160

Arg Asn Leu Tyr Leu Ile Met Glu Phe Leu Pro Gly Gly Asp Met Met
                165                 170                 175

Thr Leu Leu Met Lys Lys Asp Thr Leu Thr Glu Glu Glu Thr Gln Phe
            180                 185                 190

Tyr Ile Ser Glu Thr Val Leu Ala Ile Asp Ala Ile His Gln Leu Gly
        195                 200                 205

Phe Ile His Arg Asp Ile Lys Pro Asp Asn Leu Leu Leu Asp Ala Lys
    210                 215                 220

Gly His Val Lys Leu Ser Asp Phe Gly Leu Cys Thr Gly Leu Lys Lys
225                 230                 235                 240

Ala His Arg Thr Glu Phe Tyr Arg Asn Leu Thr His Asn Pro Pro Ser
                245                 250                 255

Asp Phe Ser Phe Gln Asn Met Asn Ser Lys Arg Lys Ala Glu Thr Trp
            260                 265                 270

Lys Lys Asn Arg Arg Gln Leu Ala Tyr Ser Thr Val Gly Thr Pro Asp
        275                 280                 285

Tyr Ile Ala Pro Glu Val Phe Met Gln Thr Gly Tyr Asn Lys Leu Cys
    290                 295                 300

Asp Trp Trp Ser Leu Gly Val Ile Met Tyr Glu Met Leu Ile Gly Tyr
305                 310                 315                 320

Pro Pro Phe Cys Ser Glu Thr Pro Gln Glu Thr Tyr Arg Lys Val Met
                325                 330                 335

Asn Trp Lys Glu Thr Leu Val Phe Pro Pro Glu Val Pro Ile Ser Glu
            340                 345                 350

Lys Ala Lys Asp Leu Ile Leu Arg Phe Cys Ile Asp Ser Glu Asn Arg
        355                 360                 365

Ile Gly Asn Ser Gly Val Glu Glu Ile Lys Gly His Pro Phe Phe Glu
    370                 375                 380

Gly Val Asp Trp Glu His Ile Arg Glu Arg Pro Ala Ala Ile Pro Ile

```
                385                 390                 395                 400
Glu Ile Lys Ser Ile Asp Asp Thr Ser Asn Phe Asp Asp Phe Pro Glu
                405                 410                 415
Ser Asp Ile Leu Gln Pro Val Pro Asn Thr Thr Glu Pro Asp Tyr Lys
                420                 425                 430
Ser Lys Asp Trp Val Phe Leu Asn Tyr Thr Tyr Lys Arg Phe Glu Gly
                435                 440                 445
Leu Thr Gln Arg Gly Ser Ile Pro Thr Tyr Met Lys Ala Gly Lys Leu
                450                 455                 460

<210> SEQ ID NO 5
<211> LENGTH: 1282
<212> TYPE: DNA
<213> ORGANISM: Homo sapiens
<220> FEATURE:
<221> NAME/KEY: CDS
<222> LOCATION: (143)...(790)
<223> OTHER INFORMATION: human MOB1

<400> SEQUENCE: 5
gcggccagaa acccggctcc gagcggcggc ggcccggctt ccgctgcccg tgagctaagg    60
acggtccgct ccctctagcc agctccgaat cctgatccag gcggggggcca ggggcccctc   120 gcctcccctc tgaggaccga ag atg agc ttc ctc ttc agc agc cgc tct tct    172
                        Met Ser Phe Leu Phe Ser Ser Arg Ser Ser
                          1               5                  10 aaa aca ttc aaa cca aag aag aat atc cct gaa gga tct cat cag tat    220
Lys Thr Phe Lys Pro Lys Lys Asn Ile Pro Glu Gly Ser His Gln Tyr
             15                  20                  25 gaa ctc tta aaa cat gca gaa gca act cta gga agt ggg aat ctg aga    268
Glu Leu Leu Lys His Ala Glu Ala Thr Leu Gly Ser Gly Asn Leu Arg
         30                  35                  40 caa gct gtt atg ttg cct gag gga gag gat ctc aat gaa tgg att gct    316
Gln Ala Val Met Leu Pro Glu Gly Glu Asp Leu Asn Glu Trp Ile Ala
     45                  50                  55 gtg aac act gtg gat ttc ttt aac cag atc aac atg tta tat gga act    364
Val Asn Thr Val Asp Phe Phe Asn Gln Ile Asn Met Leu Tyr Gly Thr
 60                  65                  70 att aca gaa ttc tgc act gaa gca agc tgt cca gtc atg tct gca ggt    412
Ile Thr Glu Phe Cys Thr Glu Ala Ser Cys Pro Val Met Ser Ala Gly
 75                  80                  85                  90 ccg aga tat gaa tat cac tgg gca gat ggt act aat att aaa aag cca    460
Pro Arg Tyr Glu Tyr His Trp Ala Asp Gly Thr Asn Ile Lys Lys Pro
                 95                 100                 105 atc aaa tgt tct gca cca aaa tac att gac tat ttg atg act tgg gtt    508
Ile Lys Cys Ser Ala Pro Lys Tyr Ile Asp Tyr Leu Met Thr Trp Val
            110                 115                 120 caa gat cag ctt gat gat gaa act ctt ttt cct tct aag att ggt gtc    556
Gln Asp Gln Leu Asp Asp Glu Thr Leu Phe Pro Ser Lys Ile Gly Val
        125                 130                 135 cca ttt ccc aaa aac ttt atg tct gtg gca aag act att cta aag cgt    604
Pro Phe Pro Lys Asn Phe Met Ser Val Ala Lys Thr Ile Leu Lys Arg
    140                 145                 150 ctg ttc agg gtt tat gcc cat att tat cac cag cac ttt gat tct gtg    652
Leu Phe Arg Val Tyr Ala His Ile Tyr His Gln His Phe Asp Ser Val
155                 160                 165                 170 atg cag ctg caa gag gag gcc cac ctc aac acc tcc ttt aag cac ttt    700
Met Gln Leu Gln Glu Glu Ala His Leu Asn Thr Ser Phe Lys His Phe
                175                 180                 185 att ttc ttt gtt cag gag ttt aat ctg att gat agg cgt gag ctg gca    748
Ile Phe Phe Val Gln Glu Phe Asn Leu Ile Asp Arg Arg Glu Leu Ala
```

-continued

```
                  190                 195                 200
cct ctt caa gaa tta ata gag aaa ctt gga tca aaa gac aga              790
Pro Leu Gln Glu Leu Ile Glu Lys Leu Gly Ser Lys Asp Arg
            205                 210                 215 taaatgtttc ttctagaaca cagttacccc cttgcttcat ctattgctag aactatctca    850
ttgctatctg ttatagacta agtgatacaa actttaagaa aacaggataa aaagatacccc   910 attgcctgtg tctactgata aaattatccc aaaggtaggt tggtgtgata gtttccgagt    970
aagaccttaa ggacacagcc aaatcttaag tactgtgtga ccactcttgt tgttatcaca   1030
tagtcatact tggttgtaat atgtgatggt taacctgtag cttataaatt tacttattat   1090
tcttttactc atttactcag tcatttcttt acaagaaaat gattgaatct gttttaggtg   1150
acagcacaat ggacattaag aatttccatc ataatttat gaataagttt ccagaacaaa    1210
tttcctaata acacaatcag attggtttta ttcttttatt ttacgaataa aaaatgtatt   1270
tttcagaaaa ag                                                        1282
```

```
<210> SEQ ID NO 6
<211> LENGTH: 216
<212> TYPE: PRT
<213> ORGANISM: Homo sapiens

<400> SEQUENCE: 6

Met Ser Phe Leu Phe Ser Ser Arg Ser Ser Lys Thr Phe Lys Pro Lys
 1               5                  10                  15

Lys Asn Ile Pro Glu Gly Ser His Gln Tyr Glu Leu Leu Lys His Ala
             20                  25                  30

Glu Ala Thr Leu Gly Ser Gly Asn Leu Arg Gln Ala Val Met Leu Pro
         35                  40                  45

Glu Gly Glu Asp Leu Asn Glu Trp Ile Ala Val Asn Thr Val Asp Phe
     50                  55                  60

Phe Asn Gln Ile Asn Met Leu Tyr Gly Thr Ile Thr Glu Phe Cys Thr
 65                  70                  75                  80

Glu Ala Ser Cys Pro Val Met Ser Ala Gly Pro Arg Tyr Glu Tyr His
                 85                  90                  95

Trp Ala Asp Gly Thr Asn Ile Lys Lys Pro Ile Lys Cys Ser Ala Pro
            100                 105                 110

Lys Tyr Ile Asp Tyr Leu Met Thr Trp Val Gln Asp Gln Leu Asp Asp
        115                 120                 125

Glu Thr Leu Phe Pro Ser Lys Ile Gly Val Pro Phe Pro Lys Asn Phe
    130                 135                 140

Met Ser Val Ala Lys Thr Ile Leu Lys Arg Leu Phe Arg Val Tyr Ala
145                 150                 155                 160

His Ile Tyr His Gln His Phe Asp Ser Val Met Gln Leu Gln Glu Glu
                165                 170                 175

Ala His Leu Asn Thr Ser Phe Lys His Phe Ile Phe Phe Val Gln Glu
            180                 185                 190

Phe Asn Leu Ile Asp Arg Arg Glu Leu Ala Pro Leu Gln Glu Leu Ile
        195                 200                 205

Glu Lys Leu Gly Ser Lys Asp Arg
    210                 215

<210> SEQ ID NO 7
<211> LENGTH: 1787
<212> TYPE: DNA
<213> ORGANISM: Mus musculus
<220> FEATURE:
```

```
<221> NAME/KEY: mRNA
<222> LOCATION: (1)...(1787)
<223> OTHER INFORMATION: mouse NDR1 mRNA

<400> SEQUENCE: 7
ggtcgcggtc gctctggagc cgcccgcacg tcgcgtctgc gccgtctctg tagccgtcgg      60
ccccgcgcct ccctccccccc tgggtctgca gccatggcaa tgacaggatc aacaccttgc    120
tcatccatga gtaatcatac gaaggagagg gtgacaatga ccaaagtgac actggagaat    180
ttttatagca accttatcgc tcaacatgaa gaacgagaaa tgagacaaaa gaagttagaa    240
aaggtgatgg aagaagaagg cctgaaagac gaagagaaac gactcagaag atccgcgcac    300
gctcggaagg aaacagagtt tcttcgatta agagaacaa ggcttggact ggaagatttt    360
gagtctttaa aagtcatagg ccgaggagca tttggtgagg tgcggcttgt tcagaagaaa    420
gacacagggc atgtgtacgc aatgaaaatc ctgcgcaaag cagacatgct cgagaaggag    480
caggttggcc acattcgtgc ggagcgtgac attctagtgg aggcagacag tttgtgggtt    540
gtgaaaatgt tctatagttt tcaggataag ctaaacctct acctaatcat ggagttcctg    600
cctggagggg acatgatgac tttattgatg aaaaaagata ctctgacaga gaggagact    660 cagttttata tagcagagac agtattagcc atagactcca ttcaccagct gggattcatc    720
cacagagata tcaagccaga caaccttctc ttggacagca agggccatgt gaaactttcc    780
gactttggcc tttgcacagg cctgaaaaaa gcacacagga cagaatttta taggaacctg    840
aaccacagcc tgcccagtga tttcactttt cagaacatga attccaaaag gaaagcagag    900
acctggaaaa gaaacagacg ccagctagcc ttctctacag tgggcactcc tgactacatt    960
gctccagagg tgttcatgca gacgggttac aacaagctct gcgattggtg gtcgctcggg    1020
gtaatcatgt acgagatgct catcggctac ccaccattct gctccagac cccacaggag    1080 acatacaaga aagtgatgaa ctggaaggaa actttgacct tcctccaga agttcctgtc    1140 tccgagaaag ccaagggcct gattctgagg ttctgctgtg aatgggaaca tagaatcgga    1200
gcccctggag ttgaagaaat aaaaaataat cttttttttg aaggtgttga ctgggaacac    1260
atcagggaga gaccagctgc gatatctatt gaaatcaaga gcatcgatga tacctcaaac    1320
ttcgatgaat ttccagagtc tgatattctt aagcccacag tgaccacaag tagtcatcct    1380
gagacggact acaagaacaa agactgggtc ttcatcaatt acacatacaa gcgcttcgag    1440
ggcctgacag ccaggggggc atacccttcg tacatgaaag cagcaaaata gggcctgtgc    1500
tgggaaccct aaatggggca gtggtctcta tacaacattg tggttttcct cttgcgctct    1560
tgaaagaact tccaagaagt ttgtagaatt cattaataca tcctagtcaa gtctctgaaa    1620
tgtgattgta agtggatatt cctccacggt gcaccgggaa gctgatagga cagagacaag    1680
cattttccca tcggccataa gcagctgctt gcttcttttg aagcccatg agccagtttg    1740 gtatgtgctg taaagagaat ttgatttccc caagttgatc agaatga              1787

<210> SEQ ID NO 8
<211> LENGTH: 2599
<212> TYPE: DNA
<213> ORGANISM: Mus musculus
<220> FEATURE:
<221> NAME/KEY: mRNA
<222> LOCATION: (1)...(2599)
<223> OTHER INFORMATION: mouse NDR2 mRNA

<400> SEQUENCE: 8
agggctcgag cggccgcccg ggcaggtaga gaatggtggg gaccccatgt ccagctgata      60
```

```
gatcatcata tcacacaggc tctggagtct agcagctttt caccaacaga gaggcgttca     120
ttgccttttt aaggacgccg gagtgggggga tcttcattct gcttttagca tgtggctgcc    180
tactactgtt tgccttacat tcttgcctgg cttcttctgg aatcttccct ggttcttccg     240 taccttttccc cacccaatct tcagactaga agtgaggcca taaaccaaga aactatgagg    300
acatccaggc tatctagctc atttggaagg agactctggc atttccagtt actatggcaa     360
tgacggcagg ggcaacaact acctttccta tgagcaacca tacccgggaa agagtaactg    420
tggccaagct cacactggag aattttttaca gcaacctaat tttacagcat gaagagagag   480
aaaccaggca gaagaagtta gaagtggcta tggaagaaga aggattagca gatgaggaga    540
aaaagttacg tcgatcgcag catgctcgta aagaaacaga gttcttacgc cttaagagga    600
ccagacttgg cctggatgac tttgagtctc tgaaggttat agcaagagga gctttcggag    660
aggtgcggct ggtccagaag aaagacacgg ggcacatcta tgccatgaag atcctgagga    720
aagctgacat gcttgagaaa gagcaggtgg ctcatatccg agcagaaagg gacattttgg    780
tggaagcaga tggagcctgg gtggtgaaga tgttctacag ttttcaggac aaacggaatc    840
tctacctcat catggaattt cttcctggag gtgacatgat gacattgctg atgaagaagg    900
acaccttaac agaagaagag acacagttct acatctcaga gactgtcttg gcgatagatg    960
caattcacca gctgggcttc atccaccggg acgtcaaacc agacaacctt ttactggatg    1020
ccaagggaca tgtaaaatta tctgattttg gtttgtgcac ggggttaaag aaagctcaca    1080
ggactgaatt ctacagaaac ctcacacata acccgccaag cgacttctca tttcagaaca    1140
tgaattcaaa gcggaaagca gagacatgga agaagaacag gagacagctg gcttactcca    1200
cagttggaac accagactac attgctccag aagtattcat gcagactggc tacaacaaat    1260
tgtgtgactg gtggtccttg ggagtgatta tgtacgagat gctaataggc tttccacctt    1320
tctgctctga acaccacaa gaaacataca gaaaagttat gagctggaag gagactctgg    1380 cattcctcc ggaagtgccc gtctctgaga aagccaagga cttgattctc agattttgta    1440
ctgattctga aaacagaatt gggaatggtg gtgtggaaga aatcaaaggt catccgttct    1500
ttgagggtgt agactgggggg cacataaggg aaagaccagc agctattcct atagaaatcc    1560
ggagtataga tgacacctca aactttgatg acttccctga gtctgatatc ttacagccag    1620
tgccgaatac cacagagccc gactacaaat ccaaagactg gttttttctc aattacacct    1680
acaaaaggtt tgaagggctg acccagagag gctccattcc tacatacatg aaagctggga    1740
agttatgatg atcacagtcg cccatagcca ggagaactca ggtagctgca tccgcaggct    1800
ggctcggcat cagcaccagg agctctggga cagtgctgct ctccagccag aggaacgact    1860
acagcttggg aatctgaggc tgctatggct atgggaattg ctcagctttt ttttttcttt    1920 ttctttttttt ttgtattaac tttattatac aaaggtactg gaacaaaaga aacagacatt    1980
ccctcctaac tgcactgcct acgtgcatgt tgagaggtcc atcctgccca tgtgctgcgc    2040
ttccgattgc aacactaatc cagccagaac tgcattgcac tgacggcacc atgacagcct    2100
gaggttgctc tcagtgtccc tgcttcactg cagagcccgt gggtctagaa tcagtgaaaa    2160
gccatcttct gtagctgctg ttagtacaac atttgccctg ttggtttgga cattgtgggc    2220
tctacatgaa gacagtttct gtaccggctc caaggaactt aaggacgctg acttcaacga    2280
cattagaatt tcctgtcagg ctctcacgca gaccctgtga tagggaagat gagcttctgt    2340
tagggtgagg gcatttctca ccttcgctcc ggcatctcca aggctgacgg tgctcacaga    2400
ttgtgacttg acgactgatg tgcacacatg gagatggacc tgaatgattg tcagctactc    2460
```

-continued

| acttttaaca | atgctgtagc | attgttttag | tttgaggatg | gtgagctgag | tttcagaaat | 2520 |
| gaccatgaaa | gctgcttgta | gaacctagta | tgtttttatt | aaacaatttt | ttttaatgtc | 2580 |
| aaaaaaaaaa | aaaaaaaaa | | | | | 2599 |

<210> SEQ ID NO 9
<211> LENGTH: 4725
<212> TYPE: DNA
<213> ORGANISM: Homo sapiens
<220> FEATURE:
<221> NAME/KEY: mRNA
<222> LOCATION: (1)...(4725)
<223> OTHER INFORMATION: human NDR2 mRNA

<400> SEQUENCE: 9

| agcggagagt | tcagggaggc | cgccctgaga | ttccggcgag | gccgcgggtc | ccacctcccg | 60 |
| ggggcgggc | gagggcggag | cggggagaag | ggagctgacg | ggcgcccggc | cggctgcggt | 120 |
| ccgtgcggag | gctgagccgg | ccgcgggcgc | gaccggaggc | agtttccgtt | actatggcaa | 180 |
| tgacggcagg | gactacaaca | acctttccta | tgagcaacca | tacccgggaa | agagtgactg | 240 |
| tagccaagct | cacattggag | aattttata | gcaacctaat | tttacagcat | gaagagagag | 300 |
| aaaccaggca | gaagaaatta | gaagtggcca | tggaagaaga | aggattagca | gatgaagaga | 360 |
| aaagttacg | tcgatcacaa | cacgctcgca | agaaacaga | gttcttacgg | ctcaaaagga | 420 |
| ccagacttgg | cttggatgac | tttgagtctc | tgaaagttat | aggaagagga | gcttttggag | 480 |
| aggtgcggtt | ggtccagaag | aaagatacag | gccatatcta | tgcaatgaag | atattgagaa | 540 |
| agtctgatat | gcttgaaaaa | gagcaggtgg | cccatatccg | agcagaaaga | gatattttgg | 600 |
| tagaagcaga | tggtgcctgg | gtggtgaaga | tgttttacag | ttttcaggat | aagaggaatc | 660 |
| tttatctaat | catggaattt | ctccctggag | gtgacatgat | gacattgcta | atgaagaaag | 720 |
| acaccttgac | agaagaggaa | acacagttct | acatttcaga | gactgttctg | gcaatagatg | 780 |
| cgatccacca | gttgggtttc | atccatcggg | atattaagcc | agacaacctt | ttattggatg | 840 |
| ccaagggtca | tgtaaaatta | tctgattttg | gtttatgtac | gggattaaag | aaagctcaca | 900 |
| ggactgaatt | ttatagaaat | ctcacacaca | acccaccaag | tgacttctca | tttcagaaca | 960 |
| tgaactcaaa | gaggaaagca | gaaacttgga | agaagaacag | gagacaactg | gcatattcca | 1020 |
| cagttgggac | accagattac | attgctccag | aagtattcat | gcagactggt | tacaacaaat | 1080 |
| tgtgtgactg | gtggtctttg | ggagtgatta | tgtatgaaat | gctaataggaa | tatccaccctt | 1140 |
| tctgctctga | aacacctcaa | gaaacataca | gaaagtgat | gaactggaaa | gaaactctgg | 1200 |
| tatttcctcc | agaggtacct | atatctgaga | agccaaggaa | cttaattctc | agattttgta | 1260 |
| ttgattctga | aaacagaatt | ggaaatagtg | gagtagaaga | aataaaaggt | catccctttt | 1320 |
| ttgaaggtgt | cgactgggag | cacataaggg | aaaggccagc | agcaatccct | atagaaatca | 1380 |
| aaagcattga | tgatacttca | aattttgatg | acttccctga | atctgatatt | ttacaaccag | 1440 |
| tgccaaatac | cacagaaccg | gactacaaat | ccaaagactg | gtttttctc | aattataccct | 1500 |
| ataaaaggtt | tgaagggttg | actcaacgtg | gctctatccc | cacctacatg | aaagctggga | 1560 |
| agttatgaat | gaagataaca | ttcacccata | accaagaaa | ctcaggtagc | tgcatcacca | 1620 |
| ggcttgcttg | gcgtagataa | caatacactg | aaatactcct | gaagatggtg | gtgcttattg | 1680 |
| actacaagag | gaaattctac | aggattagga | tttctaagac | tactatagga | attggttggc | 1740 |
| agtgccagct | ggctcttttt | tttaatattt | tattatttt | gttaacttta | ttatatgaag | 1800 |
| gtactggaat | aaaaggaaca | gacatcccctt | tctaactgca | ctgcttacat | gcgtattaag | 1860 |

```
gtccattctg cctgtgtgtg ctgtggcttt gaactgtaac acctctaatc aattcaggag    1920
gaacacatat catttaaagc aacataggct aacctgtagg taacactgca gtattgatgt    1980
tttactgcaa atcttatggg tctagataat cagtaaaagc catcttccat agttggtgtt    2040
agaacattgc cctattggtt tggacatctg tagaatatat atgaagacaa tttctgtaat    2100
ggttttaaga gatttaaaaa gaaattcact ggttctttac aaaatagaat ttatcatcaa    2160
gttattacac aaacttcaca gtaaggagtg acaagtttat aataaggaag acaaagttta    2220
acaccttcac tcaagcactc cactaatata tttacgttgc attcagaaat actgatgacc    2280
ttcatatacg tagtctgtat actcataggg agatgtactg tattatataa catgtaaagt    2340
tgattttctt gtgacaagag aacttctttt tttaacaaga ggacatggca ttattttaat    2400
ttgattatgg tgagttgaat ttaagacatg accatgaagg ctgcttgtag aattagtgta    2460
tttttattaa actatttttt taaatgtcaa acttctatca tgtaaatgga cttatagaga    2520
acaaaaagct atttactttg gttttctaga aagttgttac atatcatggc tggttaactt    2580
ttatttcttt tgatgaaaat ttttcctttg atagtacttg tattattgtg ccattatttt    2640
cttatgctcc aaatgtacca agatcttga acagagtgga tgttcacaac tgagtagaat    2700
tttcctttcc tgtgggcatg ctgtattcag acctgacaga tctttgatag aggtcagctt    2760
attaaagggc aatattgttc ttgtttagct acatcactgt ggtgaatata gatgaaatta    2820
aggaagtaaa tgcaggccag ggggttgtga tgagaggata ggggagataa tatcagcatc    2880
aaattctttg ggtatctctc taagaattaa ataatctttt ctagcttaat attttaattc    2940
taattcaaac aactctgagg ttttggtttc attagtaata gttgaggaat aatatactag    3000
caaagaatgg cctaatgttt gtcataactg ttaatggatg aaattttta aagatacaac    3060 catgataacc attataaatg atctatgatc aaaatctaaa gtgatgaatt atttgtagga    3120
atgtcttcct aatggggaag aattgcatag gagcattatg caaatctaca caagctttta    3180
taaatgttgc tgctgggtag ctccacagtg tttcataagg ccatcctgtt tcccccaact    3240
cccccatttt tggtttgttt cttttttaaat atttgttgag tacttatgtg tttatctaac    3300
agttcacttc catttttcta gtctggattt tttgagtatt taggaaagag agctattaaa    3360
aactctgggg atttctcaat gtgactaact ctaatttttc taattataac tgcctttaat    3420
taacataata ttaactttg ctgaggttta tgagattttc tcaccccaca tcgctcccct    3480
ttttttaaaa aggactgttt tgctagtgtg ataatgaata ggtaagatat gagataattg    3540
caacattgtc tagttctagt atggtaacta ttccttgaaat ggtattgaaa ataccgtta    3600 attcaaattg acagagattg ataaaaagaa actgatttac ctaagtttac ttttttaattg    3660 cataatagag catttttgt tttgagttcc ctcattctta ttaccagaaa gagcttgcaa    3720
atagttttac tttcttggca ctggaagggt agttctggaa agctactttg ttgagagtct    3780
cattcttccc tggagttaat agagtgattc acaatctttg gggttttctc ctcatcaaaa    3840
gcatttctta agtgcctatc taaaagcaat taaagactgt gtctgccctt tagaagctaa    3900 gaattttgatt catgatgcaa attaactaga taatttgcaa agtacccttg agattgaatt    3960
ttctctatta tatatttccc atatttcagg tgaataattt aatttaaatg acaaaaccct    4020
atctagtcta ctgggcataa tgacattttc tttaaattag actctatttt gaattaaaag    4080
agttttatta taaaccgtgt gttttttggtt tttctaagta tatagaaagc ttgtataatt    4140
cagatttatc aatttcctga tttaatgtag actttgactt ttttattaaa aacctttgta    4200
ttaaagcaag ttatgttatt tttcttttat gcatttatta ctaacatagc tttaaatctt    4260
```

-continued

```
taaatgtatt gaagcattgt gctgtctgaa ataaggaat tgcttataaa ccagccactt    4320
ctgaatacaa tatgtagctg atttaataag ctagttagtg aatggaaaat aagtgtggag    4380
tattaaaaat gttctttggt tggtaaggcc taagataggg tttcatttat ttctatactt    4440
tttctgtttt ttaaacacct gcatatttttt atgtaaatct ctaaatttaa aatattttaa    4500
gtacatttat ttttggtgtt ttattgtata aaaccttaga caatcaatca gtcagtcttt    4560
actgacagga gcagcagcta tctgtctttt gctgatctac aaataaatga attgagaatt    4620
tagtccatag aggtccctgg ctaccaaaca cattctcctt tgaattgtta aaattcagaa    4680
cattcaaaat aactgttttg ctacaaccca aaaaaaaaaa aaaaa                    4725
```

<210> SEQ ID NO 10
<211> LENGTH: 66
<212> TYPE: DNA
<213> ORGANISM: Artificial Sequence
<220> FEATURE:
<223> OTHER INFORMATION: synthetic oligonucleotide primer, PCR primer

<400> SEQUENCE: 10

```
cccaagcttg ccaccatggc ttacccatac gatgttccag attacgcttc gatgcaatga    60
cggcag                                                                66
```

<210> SEQ ID NO 11
<211> LENGTH: 27
<212> TYPE: DNA
<213> ORGANISM: Artificial Sequence
<220> FEATURE:
<223> OTHER INFORMATION: synthetic oligonucleotide primer; PCR primer

<400> SEQUENCE: 11

```
cgggatccct attttgctgc tttcatg                                         27
```

<210> SEQ ID NO 12
<211> LENGTH: 58
<212> TYPE: DNA
<213> ORGANISM: Artificial Sequence
<220> FEATURE:
<223> OTHER INFORMATION: synthetic oligonucleotide primer

<400> SEQUENCE: 12

```
ggacatgtgt atgcaatggc tatactccgt aaagcagata tgcttgaaaa agagcagg      58
```

<210> SEQ ID NO 13
<211> LENGTH: 65
<212> TYPE: DNA
<213> ORGANISM: Artificial Sequence
<220> FEATURE:
<223> OTHER INFORMATION: synthetic oligonucleotide primer

<400> SEQUENCE: 13

```
gcatatctgc tttacggagt atagccattg catacacatg tcccgtatct tcttctgaa    60 caagc                                                                65
```

<210> SEQ ID NO 14
<211> LENGTH: 47
<212> TYPE: DNA
<213> ORGANISM: Artificial Sequence
<220> FEATURE:
<223> OTHER INFORMATION: synthetic oligonucleotide primer

<400> SEQUENCE: 14

```
gctcggaagg aagcagagtt tcttcgtttg aagagaacaa gacttgg                  47
```

<210> SEQ ID NO 15
<211> LENGTH: 41
<212> TYPE: DNA
<213> ORGANISM: Artificial Sequence
<220> FEATURE:
<223> OTHER INFORMATION: synthetic oligonucleotide primer

<400> SEQUENCE: 15
cgaagaaact ctgcttcctt ccgagcatgt gctgatctcc g                41

<210> SEQ ID NO 16
<211> LENGTH: 44
<212> TYPE: DNA
<213> ORGANISM: Artificial Sequence
<220> FEATURE:
<223> OTHER INFORMATION: synthetic oligonucleotide sequence

<400> SEQUENCE: 16
cgtcagctag ccttcgctac agtaggcact cctgactaca ttgc             44

<210> SEQ ID NO 17
<211> LENGTH: 46
<212> TYPE: DNA
<213> ORGANISM: Artificial Sequence
<220> FEATURE:
<223> OTHER INFORMATION: synthetic oligonucleotide sequence

<400> SEQUENCE: 17
ggagtgccta ctgtagcgaa ggctagctga cgtctatttc ttttcc           46

<210> SEQ ID NO 18
<211> LENGTH: 45
<212> TYPE: DNA
<213> ORGANISM: Artificial Sequence
<220> FEATURE:
<223> OTHER INFORMATION: synthetic oligonucleotide primer

<400> SEQUENCE: 18
ggtcttcatc aattacgctt acaagcgctt tgagggcctg actgc            45

<210> SEQ ID NO 19
<211> LENGTH: 47
<212> TYPE: DNA
<213> ORGANISM: Artificial Sequence
<220> FEATURE:
<223> OTHER INFORMATION: synthetic oligonucleotide primer

<400> SEQUENCE: 19
cctcaaagcg cttgtaagcg taattgatga agacccagtc tttgttc          47

<210> SEQ ID NO 20
<211> LENGTH: 14
<212> TYPE: PRT
<213> ORGANISM: Artificial Sequence
<220> FEATURE:
<223> OTHER INFORMATION: synthetic peptide with sequence derived from
      human Ndr1 sequence
<220> FEATURE:
<221> NAME/KEY: PHOSPHORYLATION
<222> LOCATION: (8)...(9)

<400> SEQUENCE: 20

Asn Arg Arg Gln Leu Ala Phe Ser Thr Val Gly Thr Pro Asp
 1               5                  10

<210> SEQ ID NO 21
<211> LENGTH: 15

```
<212> TYPE: PRT
<213> ORGANISM: Artificial Sequence
<220> FEATURE:
<223> OTHER INFORMATION: synthetic peptide derived from human Ndr1
      sequence
<220> FEATURE:
<221> NAME/KEY: PHOSPHORYLATION
<222> LOCATION: (9)...(10)

<400> SEQUENCE: 21

Lys Asp Trp Val Phe Ile Asn Tyr Thr Tyr Lys Arg Phe Glu Gly
 1               5                  10                  15

<210> SEQ ID NO 22
<211> LENGTH: 10
<212> TYPE: PRT
<213> ORGANISM: Artificial Sequence
<220> FEATURE:
<223> OTHER INFORMATION: synthetic substrate peptide

<400> SEQUENCE: 22

Lys Lys Arg Asn Arg Arg Leu Ser Val Ala
 1               5                  10

<210> SEQ ID NO 23
<211> LENGTH: 44
<212> TYPE: DNA
<213> ORGANISM: Artificial Sequence
<220> FEATURE:
<223> OTHER INFORMATION: synthetic oligonucleotide primer

<400> SEQUENCE: 23
cttccaagct tagtcgacat ggcttaccca tacgatgttc caga              44

<210> SEQ ID NO 24
<211> LENGTH: 37
<212> TYPE: DNA
<213> ORGANISM: Artificial Sequence
<220> FEATURE:
<223> OTHER INFORMATION: synthetic oligonucleotide primer

<400> SEQUENCE: 24
ttacgcttcg gcaatgacgg cagggactac aacaacc                      37

<210> SEQ ID NO 25
<211> LENGTH: 44
<212> TYPE: DNA
<213> ORGANISM: Artificial Sequence
<220> FEATURE:
<223> OTHER INFORMATION: synthetic oligonucleotide primer

<400> SEQUENCE: 25
ggatcctcta gaggttatgg gtgaatgtta tcttcataac ttcc              44

<210> SEQ ID NO 26
<211> LENGTH: 38
<212> TYPE: DNA
<213> ORGANISM: Artificial Sequence
<220> FEATURE:
<223> OTHER INFORMATION: synthetic oligonucleotide primer

<400> SEQUENCE: 26
cgggatccgg tacccatggc aatgacggca gggactac                     38

<210> SEQ ID NO 27
<211> LENGTH: 29
<212> TYPE: DNA
<213> ORGANISM: Artificial Sequence
```

```
<220> FEATURE:
<223> OTHER INFORMATION: synthetic oligonucleotide primer

<400> SEQUENCE: 27
cgggatccct tcattcataa cttcccagc                                    29

<210> SEQ ID NO 28
<211> LENGTH: 43
<212> TYPE: DNA
<213> ORGANISM: Artificial Sequence
<220> FEATURE:
<223> OTHER INFORMATION: synthetic oligonucleotide primer

<400> SEQUENCE: 28
agcaggatcc ggtaccatgg caatgacagg ctcaacacct tgc                    43

<210> SEQ ID NO 29
<211> LENGTH: 37
<212> TYPE: DNA
<213> ORGANISM: Artificial Sequence
<220> FEATURE:
<223> OTHER INFORMATION: synthetic oligonucleotide primer

<400> SEQUENCE: 29
cgaggatcct gctccacata ggattccgtg gcaagag                           37
```

PHOSPHORYLATED NDR KINASE

CROSS REFERENCE TO RELATED APPLICATIONS

This application is a U.S. filing under 35 U.S.C. 371 of PCT/EP2003/013251 filed on Nov. 25, 2003, which claims the benefit of GB 0227562.6 filed on Nov. 26, 2002, the contents of each of which are incorporated herein by reference.

The present invention relates to a phosphorylated form of nuclear serine/threonine protein kinase, designated nuclear, Dbf2-related kinase (Ndr), and provides assays and materials for identifying modulators of Ndr kinase activity. The invention relates to the fields of molecular biology, chemistry, pharmacology, and screening technology.

Reversible protein phosphorylation is a major mechanism for the co-ordinated control of many fundamental cellular functions in eukaryotic organisms, including metabolism, growth, and differentiation. The phosphorylation status, and consequently the activity, of specific target proteins is regulated by the opposing actions of protein kinases and protein phosphatases. Generally, these enzymes are specific either for serine/threonine or for tyrosine phosphoacceptors, although some dual specificity kinases and phosphatases have also been described. The importance of phosphorylation cascades is reflected by the finding that many kinases, phosphatases, and the signal transduction pathways in which they participate have been highly conserved during the course of evolution. In recent years, interest has focused on the role of protein phosphorylation in the control of the cell cycle; a number of cellular proto-oncogenes encode members of the serine/threonine kinase family and it has become increasingly clear that certain serine/threonine kinases function as key components of the cell cycle regulatory network. Therefore, the complete delineation of these pathways is an important aim for the understanding of oncogenesis and tumour progression.

Ndr-protein kinase (also known as Pun kinase) is a nuclear serine/threonine protein kinase that is expressed in almost all cell types of the body (Millward, T. et al. (1995) *Proc. Natl. Acad. Sci. USA* 92, 5022-5026). WO 96/19579 describes the identification of Ndr kinase, an in vitro autophosphorylated form of Ndr kinase, antibodies specific for Ndr kinase, useful methods for making and using Ndr kinase, as well as other related aspects of Ndr kinase.

The NDR family of protein kinases comprises orthologous proteins such as Tricornered (trc) from *D. melanogaster*, Sax-1 from *C. elegans*, and several closely releated kinases such as Wts/Lats kinases from mammals, *D. melanogaster*, and *C. elegans*, Cbk1, Dbf2, Dbf20 from *S. cerevisiae*, Orb6 from *S. pombe*, Ukc1 from *U. maydis*, and Cot-1 from *N. crassa* (reviewed in Stegert, M. R. et al. (2001) NATO ASI Series: Protein Modules in Cellular Signalling 318, 68-80). These kinases share 40-60% amino acid identity within their catalytical domains as well as conserved regions in their regulatory domains. The Ndr subfamily of kinases has been implicated in the regulation of cell growth, cell division and cell morphology.

For example, LATS (also called Wts) was originally discovered as a gene that, when deleted, caused an overgrowth phenotype in *Drosophila*, and was thus proposed to be a tumor suppressor gene (Justice, R. W. et al. (1995) *Genes Dev.* 9, 534-546; Xu, T. et al. (1995) *Development* 121, 1053-1063). Recently, the mammalian LATS homologue was cloned, and its tumor suppressor function was confirmed. Homozygous deletion of the LATS homologue in mice causes the development of soft tissue sarcomas and ovarian stromal cell tumors (St. John, M. A. et al. (1999) *Nat. Genet.* 21, 182-186).

Other members of the Ndr kinase family have been demonstrated to be of importance in cell division. In fission yeast, Orb6 is required for the establishment of cell polarity and also appears to act as an inhibitor of Cdc2 (Verde, F. et al. (1998) *Proc. Natl. Acad. Sci. USA* 95, 7526-7531). Like Orb6, Cot-1 from *Neurospora crassa* is also required for polarized cell growth (Yarden, O. et al. (1992) *EMBO J.* 11, 2159-2166). Finally, Dbf2 is part of a pathway required for downregulation of Cdc28-cyclin B kinase activity at the end of mitosis in budding yeast (Jaspersen, S. L. et al. (1998) *Mol. Biol. Cell.* 9, 2803-2817).

The Ndr kinase subfamily is clearly important in cell growth control but it is not known how each kinase is regulated. Some members of the Ndr kinase family are known to exist as phosphoproteins (Toyn, J. H. and Johnston, L. H. (1994) *EMBO J.* 13, 1103-1113; Tao et al. (1999) *Nature Genetics* 21, 177-181). It has also been shown that NDR1 becomes potently activated by treatment of cells with the protein phosphatase 2A (PP2A) inhibitor okadaic acid (OA), indicating involvement of phosphorylation of serine and/or threonine residues in the regulation of NDR1 activity. The activation involved phosphorylation of two regulatory residues—Ser281 of the activation segment (T-loop) and Thr444 from hydrophobic motif located in the carboxyl-terminal region (Millward, T. A. et al. (1999) J. Biol. Chem. 274, 33847-33850; EP1097989, entitled "Ndr phosphokinase"). Activation of NDR1 in vitro has also been shown through a direct interaction with EF-hand Ca2+ binding protein S100B that augments NDR1 autophosphorylation (Millward, T. A. et al. (1998) EMBO J. 17, 5913-5922).

Nevertheless, there remains a need for further delineation of Ndr kinase signaling and identification of the components of the pathway.

RELEVANT LITERATURE

1. Millward, T., Cron, P., and Hemmings, B. A. (1995) Proc. Natl. Acad. Sci. U.S.A 92, 5022-5026
2. Tripodis, N., Palmer, S., Phillips, S., Milne, S., Beck, S., and Ragoussis, J. (2000) Genome Res. 10, 454-472
3. Stegert, M. R., Bichsel, S. J., and Hemmings, B. A. (2001) NATO ASI Series: Protein Modules in cellular signalling 318, 68-80
4. Geng, W., He, B., Wang, M., and Adler, P. N. (2000) Genetics 156, 1817-1828
5. Zallen, J. A., Peckol, E. L., Tobin, D. M., and Bargmann, C. I. (2000) Mol. Biol. Cell 11, 3177-3190
6. Yarden, O., Plamann, M., Ebbole, D. J., and Yanofsky, C. (1992) EMBO J. 11, 2159-2166
7. Racki, W. J., Becam, A. M., Nasr, F., and Herbert, C. J. (2000) EMBO J. 19, 4524-4532
8. Durrenberger, F. and Kronstad, J. (1999) Mol. Gen. Genet. 261, 281-289
9. Verde, F., Wiley, D. J., and Nurse, P. (1998) Proc. Natl. Acad. Sci. U.S.A 95, 7526-7531
10. Johnston, L. H., Eberly, S. L., Chapman, J. W., Araki, H., and Sugino, A. (1990) Mol. Cell Biol. 10, 1358-1366
11. Hanks, S. K., Quinn, A. M., and Hunter, T. (1988) Science 241, 42-52
12. Millward, T. A., Heizmann, C. W., Schäfer, B. W., and Hemmings, B. A. (1998) EMBO J. 17, 5913-5922
13. Millward, T. A., Hess, D., and Hemmings, B. A. (1999) J. Biol. Chem. 274, 33847-

14. Ilg, E. C., Schafer, B. W., and Heizmann, C. W. (1996) Int. J. Cancer 68, 325-332
15. Wilm, M. and Mann, M. (1996) Anal. Chem. 68, 1-8
16. Carr, S. A., Huddleston, M. J., and Annan, R. S. (1996) Anal. Biochem. 239, 180-
17. Wilm, M., Neubauer, G., and Mann, M. (1996) Anal. Chem. 68, 527-533
18. Newton, A. C. (2001) Chem. Rev. 101, 2353-2364
19. Taylor, C. W. and Broad, L. M. (1998) Trends Pharmacol. Sci. 19, 370-375
20. Treiman, M., Caspersen, C., and Christensen, S. B. (1998) Trends Pharmacol. Sci. 19, 131-135
21. Peterson, R. T. and Schreiber, S. L. (1999) Curr. Biol. 9, R521-R524
22. Parker, P. J. and Parkinson, S. J. (2001) Biochem. Soc. Trans. 29, 860-863
23. Knighton, D. R., Zheng, J. H., Ten Eyck, L. F., Ashford, V. A., Xuong, N. H., Taylor, S. S., and Sowadski, J. M. (1991) Science 253, 407-414
24. Yang, J., Cron, P., Thompson, V., Good, V. M., Hess, D., Hemmings, B. A., and Barford, D. (2002) Mol. Cell 9, 1227-1240
25. Fujisawa, H. (2001) J. Biochem. (Tokyo) 129, 193-199
26. Helerhorst, J., Kobe, B., Fell, S. C., Parker, M. W., Benian, G. M., Weiss, K. R., and Kemp, B. E. (1996) Nature 380, 636-639
27. Yamasaki, R., Berri, M., Wu, Y., Trombitas, K., McNabb, M., Kellermayer, M. S., Wltt, C., Labeit, D., Labeit, S., Greaser, M., and Granzier, H. (2001) Biophys. J. 81, 2297-2313
28. Belham, C., Wu, S., and Avruch, J. (1999) Curr. Biol. 9, R93-R96
29. Leslie, N. R., Biondi, R. M., and Alessi, D. R. (2001) Chem. Rev. 101, 2365-2380
30. Williams, M. R., Arthur, J. S., Balendran, A., van der, K. J., Poll, V., Cohen, P., and Alessi, D. R. (2000) Curr. Biol. 10, 439-448
31. Balendran, A., Hare, G. R., Kieloch, A., Williams, M. R., and Alessi, D. R. (2000) FEBS Lett. 484, 217-223
32. Yonemoto, W., McGlone, M. L., Grant, B., and Taylor, S. S. (1997) Protein Eng 10, 915-925
33. Le Good, J. A., Ziegler, W. H., Parekh, D. B., Alessi, D. R., Cohen, P., and Parker, P. J. (1998) Science 281, 2042-2045
34. Hill, M. M., Andjelkovic, M., Brazil, D. P., Ferrari, S., Fabbro, D., and Hemmings, B. A. (2001) J. Biol. Chem. 276, 25643-25646
35. Hill, M., Feng, J., and Hemmings, B. (2002) Curr. Biol. 12, 1251
36. Delcommenne, M., Tan, C., Gray, V., Rue, L., Woodgett, J., and Dedhar, S. (1998) Proc. Natl. Acad. Sci. U.S.A 95, 11211-11216
37. Alessi, D. R., Andjelkovic, M., Caudwell, B., Cron, P., Morrice, N., Cohen, P., and Hemmings, B. A. (1996) EMBO J. 15, 6541-6551
38. Lynch, D. K., Ellis, C. A., Edwards, P. A., and Hiles, I. D. (1999) Oncogene 18, 8024-8032
39. Shaw, M., Cohen, P., and Alessi, D. R. (1998) Biochem. J. 336, 241-246
40. Ziegler, W. H., Parekh, D. B., Le Good, J. A., Whelan, R. D., Kelly, J. J., Frech, M., Hemmings, B. A., and Parker, P. J. (1999) Curr. Biol. 9, 522-529
41. Romanelli, A., Martin, K. A., Toker, A., and Blenis, J. (1999) Mol. Cell Biol. 19, 2921-2928
42. Akimoto, K., Nakaya, M., Yamanaka, T., Tanaka, J., Matsuda, S., Weng, Q. P., Avruch, J., and Ohno, S. (1998) Biochem. J. 335, 417-424
43. Behn-Krappa, A. and Newton, A. C. (1999) Curr. Biol. 9, 728-737
44. Haby, C., Larsson, O., Islam, M. S., Aunis, D., Berggren, P. O., and Zwiller, J. (1994) Biochem. J. 298, 341-346
45. Hepworth, T. J., Lawrie, A. M., and Simpson, A. W. (1997) Cell Calcium 21, 461-467.
46. Berridge, M. J., Lipp, P., and Bootman, M. D. (2000) Nat. Rev. Mol. Cell Biol. 1, 11-21.

BRIEF DESCRIPTION OF THE SEQUENCE LISTING

SEQ ID NO:1 provides the nucleotide sequence and amino acid sequence of human NDR1
SEQ ID NO:3 provides the nucleotide sequence and amino acid sequence of human NDR2
SEQ ID NO:5 provides the nucleotide sequence and amino acid sequence of human MOB1
SEQ ID NO:7 provides the nucleotide sequence of mouse NDR1 mRNA
SEQ ID NO:8 provides the nucleotide sequence of mouse NDR2 mRNA
SEQ ID NO:9 provides the nucleotide sequence of human NDR2 mRNA

SUMMARY OF THE INVENTION

The present invention relates to nuclear, Dbf2-related (Ndr) phosphokinase, a functional homologue thereof or fragment thereof, wherein the polypeptide is phosphorylated at amino acid Thr-74 or an amino acid corresponding to amino acid Thr-74 of Ndr protein kinase 1 (SEQ ID NO:1), or said amino acid is replaced by an acidic amino acid residue. The polypeptide may further comprises phosphorylation at Ser-281 and/or Thr-444. The homologue typically comprises a sequence having 50% or more identity to the amino acid sequence set forth in SEQ ID NO:1 and at least one peptide defined by the sequence: -K-E-S/T-E-F/Y-.

Furthermore, the present invention relates to an antibody that specifically binds to Ndr kinase or a functional homologue thereof, wherein the polypeptide is phosphorylated at amino acid Thr-74 or an amino acid corresponding to amino acid Thr-74 of Ndr protein kinase 1 (SEQ ID NO:1) and the antibody recognizes an epitope comprising the phosphorylated amino acid. The antibody can be polyclonal or monoclonal, or genetically engineered. Also encompassed by the invention is the use of the antibodies of the invention to detect or isolate Ndr polypeptides or their homologues, or as a diagnostic or therapeutic, in particular in the treatment of abnormalities in cellular proliferation.

The present invention also relates to a method of isolating a polypeptide selected from the group consisting of nuclear, Dbf2-related (Ndr) kinase, a functional homologue thereof or a fragment thereof, wherein the polypeptide is phosphorylated at Thr-74 or an amino acid corresponding to amino acid Thr-74 of Ndr protein kinase 1 (SEQ ID NO:1), by contacting the polypeptide with an antibody of the invention and removing contaminating materials. Optionally, the method further comprises treating cells containing a nucleic acid encoding the polypeptide with okadaic acid, allowing the cells to express the polypeptide and preparing a cell extract from the cells.

In another aspect the invention relates to the use of the polypeptides of the invention for the identification of an agonist or antagonist of Ndr kinase activity.

In a further aspect the invention relates to the polypeptides of the invention for use as a medicament.

In a yet further aspect the invention relates to the use of the polypeptides of the invention for the manufacture of a medicament for the treatment of abnormalities in cellular proliferation.

In another aspect the invention relates to a complex comprising the polypeptide of the invention with MOB1, where optionally one or more of the proteins can be labelled, e.g., fluorescently labelled.

In another aspect the invention relates to a method for screening potential modulators of Ndr kinase activity, said method comprising the steps of a) incubating a polypeptide of the invention with a potential modulator and b) detecting an interaction between the modulator and the polypeptide.

The present invention also relates to a method for screening potential modulators of Ndr kinase activity, said method comprising the steps of a) incubating a polypeptide of the invention with the potential modulator and b) detecting a change in phosphorylation of the polypeptide at Thr74 or an amino acid corresponding to amino acid Thr-74 of Ndr protein kinase 1. In this embodiment, the potential modulator can be a kinase of a signalling pathway, for example.

The present invention also provides a method for screening for potential modulators of Ndr kinase activity, said method comprising the steps of: a) incubating a complex of the invention with a potential modulator; and b) detecting a change in binding between MOB1 and the Ndr polypeptide. The potential modulator may decrease binding to release MOB1. Alternatively, the potential modulator may increase or stabilize binding, in particular where the modulator is a MOB1 fragment or derivative.

Furthermore, the present invention relates to a kit comprising the polypeptides and/or antibodies of the invention and instructions. The kit may further comprise MOB1, optionally with antibodies recognizing MOB1.

DETAILED DESCRIPTION OF THE INVENTION

The present inventors have characterized in detail the regulation of NDR by phosphorylation of two regulatory residues Ser281 and Thr444, and its activation through a direct interaction with EF-hand Ca2+-binding proteins of the S100 family. As a result, they uncovered an additional regulatory phosphorylation site on NDR1, namely Thr74. All three amino acid residues are crucial for NDR1 activity in vivo; however, in contrast to Ser281 and Thr444, Thr74 is involved in binding to regulatory proteins (e.g., S100B) rather than directly regulating NDR1 activity per se. The numbers assigned to these residues reflect their position within the human Ndr1 kinase sequence as provided in WO 96/19579 (see also SEQ ID NO:1). In addition, the present inventors have identified and characterized a second isoform of human Ndr protein kinase, termed NDR2, which is regulated in a similar manner as NDR1 and exhibits kinase activity that is dependent on the phosphorylation of the conserved phosphorylation sites Ser282 and Thr442, as well as Thr75. The sequence of Ndr2 is provided in SEQ ID NO:3.

Thus, in its broadest aspect, the present invention is directed to an isolated polypeptide, wherein said polypeptide is nuclear, Dbf2-related (Ndr) phosphokinase as set forth in the amino acid sequence of SEQ ID NO:1, a functional homologue thereof or a fragment thereof, and wherein said polypeptide is phosphorylated at Thr-74 or an amino acid corresponding to amino acid Thr-74 of Ndr protein kinase 1.

Homologues are polypeptides that share sufficient similarities for the skilled person to determine that they share homology of origin or function with the Ndr protein kinases as represented by human Ndr2 (SEQ ID NO:3), provided that the homologue is phosphorylated at Thr-74 or an amino acid corresponding to amino acid Thr-74 of Ndr protein kinase 1, such as Thr-75 of hNdr2 or a serine/threonine residue at a corresponding position in other homologues (equivalent), or this particular phosphorylation site is replaced by an acidic amino acid residue. The invention includes all species homologues of Ndr from other organisms modified in this way, such as *Drosophila* Ndr, represented in SEQ ID No. 2 of WO 96/19579, which may be isolated according to conventional methods. Species homologues of Ndr may be considered derivatives of the polypeptide sequences set out herein. A "functional homologue" of Ndr kinase encompasses derivatives and analogues of these homologous polypeptides, including any single or multiple amino acid additions, substitutions and/or deletions occurring internally or at the amino or carboxy termini thereof—so long as Ndr biological activity remains. That is, a functional homologue may be devoid of a certain domain or connected to another polypeptide, e.g., in the form of a fusion protein. A mutant according to the invention still reacts comparably to the natural Ndr, as desired, e.g., in respect to the enzymatic activity or specificity, or protein binding.

Thus, a functional homologue includes functional fragments of the polypeptide, as long as the biological activity of the polypeptide remains and the homologue or fragment maintains a phosphorylated Thr-74 (or equivalent). Fragments of Ndr comprise the Ndr polypeptide, or a mutant (or homologue) thereof, in which a substantial part of the polypeptide has been removed. Fragments of Ndr may have a substantially different activity to natural Ndr, or indeed lack one of the native Ndr biological activities. Thus, Ndr fragments may comprise an individual Ndr kinase domain, or a subset of Ndr kinase domains, as well as the S100B binding domain. Ndr contains all of the 12 protein kinase catalytic subdomains identified by Hanks and Quinn (Meth. Enzymol. (1991) 200, 38-62). Of these, the presence of subdomains VIb and VIII suggest that Ndr is a serine/threonine kinase. Thus, the invention includes homologues comprising any subset of the kinase domains of Ndr, especially the serine/threonine kinase domains. In addition, it has been found that the amino acids 265-276 (KRKAETWKRNRR) of the human Ndr code for a nuclear localisation signal. Accordingly, the current invention also comprises a fragment of Ndr comprising a nuclear localisation signal and having the amino acid sequence KRKAETWKRNRR.

Smaller peptides containing the biological activity of polypeptide are included in the invention. Smaller peptides comprising the Thr 74 site (or equivalent) will be at least 5 amino acids long and preferably comprise consecutive amino acids selected from the native amino acid sequences. Preferred peptides are typically 6-15 amino acids long, depending on their projected use, with peptides of 8-10 amino acids long preferred for the production of antibodies, and peptides of 6-10 or 6-15 amino acid long as phosphatase substrates, for example.

As used herein, the term "Ndr biological activity" is not limited to the ability of Ndr kinase to phosphorylate a substrate but also includes other characteristics of the protein or peptide, such as, the ability to bind an antibody specific for Ndr kinase phosphorylated at Thr-74 or its equivalent (i.e., differentiate between the phosphorylated and non-phosphorylated state of Ndr kinase), or its ability to bind to a substrate or a modulator of Ndr kinase, including proteins such as S100B or MOB1.

In a preferred case, homology is used herein to refer to sequence identity. Thus, homologues are also polypeptides that share a certain amount of sequence identity with the Ndr protein kinases as herein described. The sequence identity is typically 50% or more, preferably 60% or more and more preferably 75% or more, most preferably 90% or more. Human and *Drosophila* Ndr sequences share 68% sequence identity. Dbf2, on the other hand, possesses only 32% overall amino acid identity with human Ndr, suggesting that Dbf2 is related to Ndr, but that the two are not species homologues. Where amino acid residues in members of the Ndr protein kinase family are not identical, the homologue preferably comprises conservative substitutions or alterations that do not alter the structure/function relationship of the kinase domain(s) of interest. Any substitution of Ser-281, Thr-444, Thr-74 or their corresponding phosphorylation sites in homologues will preferably be with acidic amino acid residues, such as glutamate, unless it is desired to ablate the function attributed to the phosphorylation site, e.g., substitution with alanine as a negative control. Preferably, homologues comprising Thr-74, Ser-281 and/or Thr-444 will be phosphorylated at these sites, although homologues comprising only the Thr-74 phosphorylation site will be useful, for example, for binding activity with interacting proteins.

Particularly preferred homologues are those comprising the sequence -K-E-S/T/N-E-F/Y-, where N is an acidic amino acid, S and T refer to phosphoserine or phosphothreonine residue and the remaining amino acids are described by their conventional one letter codes, and most preferred homologues are those comprising -K-E-S/T-E-F/Y-. The preferred homologues may further comprise at least one of the sequences -Arg-Xaa-Leu/Met-Ala-Xaa-$P_1$-Xaa-Val-Gly-Thr-Pro-Xaa-Tyr-Ile-Ala-Pro-Glu- or -Phe-Xaa-Xaa-Xaa-$P_2$-Xaa-Xaa-Xaa-Phe-, where "/" indicates alternative amino acid residues, $P_1$ and $P_2$ refer to phosphorylated amino acid or acidic amino acid residues, preferably phosphoserine and phosphothreonine, respectively, Xaa can be any amino acid and the remaining amino acids are described by their conventional three letter codes. In a more preferred embodiment, the homologues comprise at least one of -Arg/Gln-Arg-Gln/Val/Leu-Leu/Met-Ala-Phe/Tyr/His-$P_1$-Thr/Leu-Val-Gly-Thr-Pro-Asp/Asn-Tyr-Ile-Ala-Pro-Glu- or -Phe-Ile/Leu/Phe-Glu/Gly/Asn-Phe/Tyr-$P_2$-Phe/Tyr-Lys/Arg-Lys/Arg-Phe-, where where "/" indicates alternative amino acid residues, $P_1$ and $P_2$ refer to phosphorylated amino acid or acidic amino acid residues, preferably phosphoserine and phosphothreonine, respectively, and the remaining amino acids are described by their conventional three letter codes.

If the polypeptide of the invention is expressed in the form of a fusion protein, the fused polypeptides may be connected directly or by a spacer. It is for example possible to insert, if not already naturally present, a region that can be specifically recognised and cleaved chemically or enzymatically. Examples for selective cleaving reagents or enzymes are CNBr, V8 protease, trypsin, thrombin, factor X, peptidase ysca and yscF. The fused polypeptide may comprise sequences useful for isolating the protein such as "tags" (e.g., His tags or HA tags) or may be linked to unrelated sequences such as marker protein, e.g., fluorescent proteins or enzymes, e.g., beta-galactosidase, as is well known in the art.

Methods for the construction of fusion proteins, mutations or fragments by recombinant or chemical techniques are known in the art.

In a further aspect of the invention, antibodies specific for Ndr kinase phosphorylated at Thr 74 (or equivalent) are provided. As described above, such antibodies are able to differentiate between the phosphorylated and non-phosphorylated forms of Ndr kinase. Such antibodies can be polyclonal, monoclonal, antibody fragments (Fc, Fv), and from any source, e.g., mouse, rat, goat, human, recombinant, etc. Such antibodies may be useful for identifying, detecting or isolating Ndr, for example by immunostaining, immunoprecipitation or immunoseparation, or for disrupting Ndr activity in vivo or in vitro.

Antibodies specific for Ndr phosphorylated at Thr 74 (or equivalent) may be prepared according to techniques known in the art. In order to prepare a polyclonal serum, for example, an antigenic portion of Ndr kinase comprising phosphorylated Thr74, optionally in the presence of an adjuvant or conjugated to an immunostimulatory agent such as keyhole limpet haemocyanin, is injected into a mammal such as a mouse or a rabbit and antibodies are recovered therefrom by affinity purification using a solid-phase bound kinase or antigenic portion thereof. Monoclonal antibodies may be prepared according to similar established procedures.

Phosphorylation of Ndr kinase can be induced in cells expressing Ndr by treatment with okadaic acid. The cells may naturally express Ndr kinase or may comprise an expression vector comprising the Ndr kinase coding sequence. Thus, the methods are amenable to use in a variety of host cells. Methods of expressing and isolating Ndr kinase from cell extracts are well known in the art (see, for example, WO 96/19579). Antibodies specific for Ndr phosphorylated at Thr 74 (or equivalent) are particularly useful in isolating Ndr kinase or its homologues phosphorylated at this site, for example, using affinity chromatography or immunoprecipitation to separate the desired protein from contaminating materials, as is well known in the art.

The polypeptide, and especially its derivatives, may be obtained by synthetic means rather than derived from natural sources. Thus, using the information contained herein, Ndr polypeptide or peptides may be synthesised using commercially available protein synthesisers or even ordered from a commercial peptide synthesis service. Synthesised derivatives of Ndr may comprise any desired sequence modifications, including the use of altered amino acid residues or the addition of heterologous groups or side-chains to the polypeptide. The polypeptides or peptides may then be phosphorylated in vitro, as described in the Examples below.

The present inventors have also examined the interaction of NDR with hMOB1 and found that hMOB1 interacts with hNDR in an okadaic acid stimulation dependent manner (see Example 8). Overexpression of hMOB1 also stimulates NDR kinase activity. Point mutation of conserved residues within the N-terminal regulatory domain of NDR reduces NDR kinase activity as well as MOB1 binding. The NDR-MOB interaction is affected by an okadaic acid induced modification of MOB1, while okadaic acid induced phosphorylation of NDR is not required for the interaction. Treatment of cells with the Ca2+ chelator BAPTA-AM reduces NDR-MOB interaction, pointing to a role of Ca2+ in the NDR-MOB interaction.

Thus, in a further aspect of the invention a complex comprising Ndr, its functional homologues or fragments and MOB1 (MPS one binder 1) is provided. The sequence of hMOB1 is provided in GI: 11691898 and in SEQ ID NO:5 below and as will be apparent to those of ordinary skill in the art, homologues of MOB1 may also bind to Ndr. MOB1 homologues are polypeptides that share a certain amount of sequence identity with the MOB1 sequence provided in GI 11691898 or SEQ ID NO:5 or 6. The sequence identity is typically 50% or more, preferably 60% or more and more preferably 75% or more, most preferably 90% or more. Preferably, the proteins are human proteins. In some embodiments, one or more of the proteins are labelled for ease of detection, such as by using a fluorescent label. Thus, interactions between the two proteins (e.g., Ndr1 and Mob1) can be detected by the amount of fluorescent label bound or by fluorescence quenching.

Kinases such as Ndr are known to be involved in signal transduction within cells. This involvement makes kinases targets for agents that modulate signalling pathways. Typically, modulation of a signalling pathway will alter the response of a cell to a particular stimulus. For example, the effect of hormones may be modulated by targeting the kinases involved in signal transduction from the hormone receptor to the biological effectors, which are typically regulators of gene expression. The S100 family of proteins represent the principle calcium ion binding proteins in the cell and are involved in many calcium-mediated effects. The activity of Ndr is regulated in particular by S100B.

The polypeptides of the invention are useful for the identification of an agonist or antagonist of Ndr kinase activity, and potentially as a medicament, such as in the treatment of abnormalities in cellular proliferation. Preferably, the screening methods of the invention comprise bringing a cell into contact with an activator or an inhibitor of Ndr. Activators and inhibitors, which include Ndr mimics and are referred to collectively as modulators, interact with Ndr at or near the Thr 74 site, thereby influencing the effect of Thr 74 phosphorylation on Ndr activity. Alternatively, modulators may act on MOB1, blocking or enhancing its binding to the Thr 74 region of Ndr, thereby activating or repressing the activity of Ndr by other means.

Thus, in one aspect of the invention, a method for identifying potential modulators of Ndr kinase activity is provided by contacting Ndr kinase or a functional homologue thereof with a potential modulator; and detecting a change in phosphorylation at Thr74 of the Ndr kinase or an amino acid corresponding to amino acid Thr-74 of Ndr protein kinase 1 or the functional homologue thereof. A change in phosphorylation can easily be detected using phospho-specific antibodies. A decrease in phosphorylation at Thr 74 is indicative of a compound that inhibits Ndr kinase activity.

In an alternative embodiment, a method for identifying potential modulators of Ndr kinase activity is provided by contacting Ndr phosphorylated at Thr 74 (or equivalent) or a functional homoloqgue thereof with a potential modulator; and detecting interaction between the modulator and the phosphorylated Ndr or the functional homologue thereof. Such modulators can include without limitation agonists, antagonists and upstream members of a signaling pathway.

In a further embodiment, the invention provides a method for screening for potential modulators of Ndr kinase activity comprising the steps of incubating a protein complex of MOB1 and Ndr (or homologues or fragments thereof) with the potential modulator; and detecting a change in binding between the MOB and the polypeptide. Thus, the modulator can result in a decreased binding between the two proteins to release MOB1, in which case NDR kinase activity is inhibited (unless the modulator is a functional fragment of MOB1 with higher affinity for NDR than the full length MOB1, in which case the MOB1 functional fragment could mimic MOB1 activity and activate Ndr activity). Alternatively, the modulator can result in an increased binding between the two polypeptides, thereby activating Ndr activity.

The Ndr kinase materials of the invention can therefore be used in the design of screening systems to identify putative therapeutic agents for use in treating anomalies in growth control. WO 97/18303 hereby incorporated by reference describes screening methodologies, kits, potential therapeutic agents and their formulation, the teachings of which can be applied to the materials and methods of the present invention.

For binding studies, the polypeptide of the invention may be, for example, immobilised on a solid carrier like a microtiter plate or beads; or may bear one or more identifiable markers like biotin or a radioactive, fluorescent or chemiluminescent group. In a preferred embodiment of the present invention, Ndr 1 or 2 is used in a method for screening potential modulators of Ndr activity.

Incubation conditions will vary according to the precise method used to assay, for example using a kinase assay or detection of the interaction between the kinase and the screened compound. In the case of transcription activation detection systems such as the yeast two-hybrid system, incubation conditions are suitable for gene transcription, such as those prevailing inside a living cell. Other detection systems, however, will require different incubation conditions. For example, if the detection of interaction is based on relative affinity in a chromatographic assay, for example as is known in affinity chromatography, conditions will be adjusted to promote binding and then gradually altered, such that the point at which the screened compound no longer binds to Ndr may be determined.

Incubation according to the invention may be achieved by a number of means, but the basic requirement is for the kinase or a homologue/fragment thereof and the screened compound to be able to come into contact with each other. This may be achieved by admixing the polypeptide and the compound, or by producing them in situ, such as by expression of nucleic acids encoding them. Where Ndr or the Ndr fragment and/or the compound are in the form of fusions with other polypeptides, they may be expressed as such in situ.

Ndr or a homologue or fragment thereof according to the invention may be used to screen for compounds which bind thereto by incubating it with the compound to be screened and subsequently "pulling down" Ndr complexes with an Ndr-specific antibody or MOB1 specific antibody, for example. Antibodies suitable for immunoprecipitation or immuno-affinity chromatography may be prepared according to conventional techniques, known to those of ordinary skill in the art, and may be monoclonal, polyclonal or recombinant in nature. After the Ndr-compound complex has been isolated by affinity, the compound may be dissociated from the Ndr antibody and characterised by conventional techniques.

The invention further comprises the use of Ndr phosphorylated at Thr 74 (or equivalent) or Ndr having an acidic amino acid at this residue in a screening system.

In a still further embodiment, the invention provides a compound that interacts directly or indirectly with Ndr (or MOB1) or a fragment thereof. Such a compound may be inorganic or organic, for example an antibiotic or a proteinaceous compound involved in intracellular signalling.

Compounds according to the invention may be identified by screening using the techniques described hereinbefore, and prepared by extraction from natural sources according to established procedures, or by synthesis, especially in the case of low molecular weight chemical compounds. Proteinaceous compounds may be prepared by expression in recombinant expression systems, for example a baculovirus system, or in a bacterial system. Proteinaceous compounds are mainly useful for research into the function of signalling pathways, although they may have a therapeutic application.

Low molecular weight compounds, on the other hand, are preferably produced by chemical synthesis according to established procedures. They are primarily indicated as therapeutic agents. Low molecular weight compounds and organic compounds in general may be useful as antiproliferative agents.

Thus, Ndr kinase phosphorylated at The 74 (or equivalent) or its functional homologues can be useful as medicaments or for preparing medicaments, in particular for the treatment of abnormalities in cellular proliferation, such as cancer, diseases or disorders of the immune system (e.g., immunodeficiencies) and neurodegenerative diseases.

Kits useful for screening such compounds may be prepared, and will comprise essentially Ndr phosphorylated at Thr 74 (or equivalent) or a functional homologue thereof with instructions, optionally comprising one or more of a means for detecting an interaction between Ndr and the screened compound, MOB1 or homologues thereof, and a means for detecting an interaction between MOB1 and the screened compound. Preferably, therefore, the screening kit comprises one of the detection systems set forth hereinbefore.

Ndr for use in kits according to the invention may be provided in the form of a protein, for example in solution, suspension or lyophilised, or in the form of a nucleic acid sequence permitting the production of Ndr or a fragment thereof in an expression system.

The following examples describe specific aspects of the invention to illustrate the invention and provide a description of the present method for those of skill in the art. The examples should not be construed as limiting the invention, as the examples merely provide specific methodology useful in understanding and practice of the invention.

EXAMPLES

Methodology

Standard methods in genetic engineering like random priming, subcloning, sequencing, cleavage with restriction enzymes, gel purification, ligations, transformation and annealing are carried out essentially as described in Sambrook et al., Molecular Cloning: A laboratory manual, $2^{nd}$ Edn. Cold Spring Harbor Laboratory Press, Cold Spring Harbor N.Y., 1989.

Cell Culture

COS-1 cells were maintained in Dulbecco's modified Eagle's medium containing 10% FCS, 100 U/ml penicillin and 100 microg/ml streptomycin. Cells were transfected at subconfluent stage with Fugene-6 transfection reagent (Roche) according to manufacturer's instructions.

In some experiments, the cells were treated for 60 min with 1 microM okadaic acid in 0.1% N,N-dimethylformamide (DMF) (Alexis Corp.), 50 microM BAPTA-AM (1,2-bis (o-aminophenoxy) ethane-N,N,N',N'-tetraacetic acid tetra (acetoxy-methyl)ester) in 0.1% diimethylsulfoxide (DMSO; Sigma), or 20 microM thapsigargin in 0.1% DMSO (Alomone) 24 hours after transfection.

Plasmids

A mammalian expression vector with HA-tagged NDR1 was constructed by PCR using the following primers:
5'-CCCAAGCTTGCCACCATGGCTTACCCAT-ACGATGTTCCAGATTACGCTTCGATGCAA TGACG-GCAG-3' (SEQ ID NO:10) and 5'-CGGGATC-CCTATTTTGCTGCTTTCATG-3' (SEQ ID NO:11), and subcloned into the HindIII and BamHI sites of pCMV5. pGEX-2T_NDR1 plasmid has been described previously (Millward et al., 1995, Proc. Natl. Acad. Sci. U.S.A 92, 5022-5026). The pCMV5_HA-NDR1 and pGEX-2T_NDR1 plasmids for kinase dead (K118A) and phosphorylation-site alanine mutants (T74A, S281A and T444A) were generated from wild-type vectors using QuickChange site mutagenesis protocol (Stratagene) with following primers:
5'-GGACATGTGTATGCAATGGCTATACTC-CGTAAAGCAGATATGCTTGAAAAAGAGCAG G-3' (SEQ ID NO:12) and 5'-GCATATCTGCTTTACGGAG-TATAGCCATTGCATACACATGT CCCGTATCTTTCT-TCTGAACAAGC-3' (K 118A; SEQ ID NO:13); 5'-GCTCGGAAG-GAAGC AGAGTTTCT-TCGTTTGAAGAGAACAAGACTTGG-3' (SEQ ID NO:14) and 5'-CGAAG AAAC-TCTGCTTCCTTC-CGAGC-ATGTGCTGATCTCCG-3' (T74A; SEQ ID NO:15); 5'-CGTCAGCTAGCCTTC-GCTACAGTAG-GCACTCCTGACTACATTGC-3' (SEQ ID NO.16) and 5'-GGAGTGCCTACTGTAGCGA-AGGCTAGCT-GACGTCTATTTCTTTTCC-3' (S281A; SEQ ID NO:17); and 5'-GGTCTTCATCAATTAC-GCTTA-CAAGCGCTTTGAGGGCCTGA CTGC-3' (SEQ ID NO:18) and 5'-CCTCAAAGCGCTTGTAA-GCGTAAT-TGATGAAGACC CAGTCT-TTGTTC-3' (T444A; SEQ ID NO:19).

pECE_S100B plasmid has been described previously (Millward et al., 1998, EMBO J. 17, 5913-5922). The sequence of all plasmids was confirmed by DNA sequencing.

Antibodies

Anti-Ser281P and anti-Thr444P rabbit polyclonal antisera were raised against the synthetic peptides NRRQLAFS($PO_4$) TVGTPD (SEQ ID NO:20) for the Ser281P site and KDWVFINYT($PO_4$)YKRFEG (SEQ ID NO:21) for the Thr444P site. The peptides had been conjugated to keyhole limpet hemocyanin. Rabbit injections and bleed collections were carried out using standard techniques. The anti-S281P antiserum was used without further purification whereas the anti-T444P antibody was purified on protein A-Sepharose (Pharmacia) followed by antigenic peptide coupled to CNBr-activated Sepharose (Pharmacia). Antibodies were eluted with 0.1 M Glycine, pH 2.5. The12CA5 HA monoclonal antibody hybridoma supernatant (an antibody specific for HA) was used for immunodetection and immunoprecipitation of HA-NDR1 variants. A rabbit anti-NDR1_C-term polyclonal antiserum was raised against a synthetic peptide TARGAIPSYMKAAK (corresponding to NDR1 aa452-465 of SEQ ID NO:2) conjugated to keyhole limpet hemocyanin. Peptide specific antibodies were purified on protein A-Sepharose (Amersham Pharmacia Biotech) followed by Affi-Gel 10 (Bio-Rad) with coupled immunopeptide. Antibodies were eluted with 50 mM Tris-HCl, pH 7.4 containing 6M urea and dialyzed subsequently against phosphate-buffered saline (PBS). A rabbit polyclonal antiserum which recognizes S100B was raised against recombinant human S100B, and was used without further purification (Ilg et al., 1996, Int. J. Cancer 68, 325-332).

Bacterial Expression of Human GST-Fused NDR1

BL21-DE3-pRep4 E. coli strain was transformed with the pGEX-2T_NDR1 wild type or mutant plasmids. BL21-DE3 is a protease-deficient E. coli strain and pRep4 is a Laclq repressor-bearing plasmid both available commercially. Optionally, if desired, an E. coli strain comprising GroESL can be used, which expresses a chaperone protein that stabilizes the kinase. Mid-logarithmic phase cells were induced with 0.5 mM isopropyl beta-D-thiogalactopyranoside (IPTG) for 4 hours at 30° C. Bacteria were lysed using a French press in the presence of 1 mg/ml lysosyme, and the fusion proteins were purified on glutathione-agarose (Amersham Pharmacia Biotech) as described by the manufacturers. Recombinant proteins were assayed for kinase activity as described below and autophosphorylation was determined after SDS-PAGE separation either by Cerenkov counting or by exposure to a PhosphorImager screen followed by analysis with ImageQuant software (Molecular Dynamics).

GST-NDR1 Kinase Assay 1 microgram of purified recombinant GST-NDR1 wild type and mutants (without further treatment or autophosphorylated for 2 h in the presence or absence of 1 mM $CaCl_2$ and 10 mM bovine S100B (Sigma)) were assayed in 20 microliter of reaction mixture containing 20 mM Tris-HCl pH 7.5, 10 mM $MgCl_2$, 1 mM DTT, 100 microM [gamma-$^{32}$P]ATP (~0.5 microCi/microliter), and 1 mM NDR1 substrate peptide (KKRNRRLSVA; SEQ ID NO:22). After 30 mins incubation at 30° C., reactions were stopped with 50 mM EDTA, and 10 microliters of reaction mixture were spotted onto 2 $cm^2$ squares of P81 phosphocellulose paper (Whatman). These were subsequently washed for 4×5 min and 3×20 min in 1% phosphoric acid and once in acetone before counting in a liquid scintillation counter. One unit of NDR1 activity was defined as the amount which catalyses the phosphorylation of 1 nmol peptide substrate in 1 min.

HA-NDR1 Kinase Assay

Transfected and treated COS-1 cells were washed once with ice-cold PBS, and harvested by rubber policeman in 1 ml ice-cold PBS containing 1 mM $Na_3VO_4$ and 20 mM beta-glycerophosphate before lysis in 500 microliters of IP buffer (20 mM Tris-HCl pH 8.0, 150 mM NaCl, 1% Nonidet P-40, 10% glycerol, 1 mM $Na_3VO_4$, 20 mM beta-glycerolphosphate, 1 microM microcystin-LR, 50 mM NaF, 0.5 mM PMSF, 4 microM leupeptin, 1 mM benzamidine, and 1 tablet/10 ml IP of Complete protease inhibitors (Roche)). Lysates were centrifuged at 20 000 g for 20 min and triplicate aliquots (200 microg) of supernatant were precleared with protein A-Sepharose (Amersham Pharmacia Biotech) for 60 min and mixed subsequently for 3 h at 4° C. with 12CA5 antibody prebound to protein A-Sepharose (~1 microg antibody bound to 2 microl beads). The beads were then washed twice with IP buffer, once for 10 min with IP buffer containing 1 M NaCl, once again for 10 min with IP buffer, and finally twice with 20 mM Tris-HCl pH 7.5 containing 4 microM leupeptin and 1 mM benzamidine. Thereafter, beads were resuspended in 30 microliters buffer containing 20 mM Tris-HCl pH 7.5, 10 mM $MgCl_2$, 1 mM DTT, 100 microM [gamma-$^{32}$P]ATP (~0.1 microCi/microliter), 1 microM cAMP-dependent protein kinase inhibitor peptide PKI (Bachem), 4 microM leupeptin, 1 mM benzamidine, 1 microM microcystin-LR, and 1 mM NDR1 substrate peptide (KKRNRRLSVA). After 60 min incubation at 30° C., 15 microliters of supernatant were removed, and phosphate incorporation into the substrate peptide determined as described for GST-NDR1 above.

Immunodetection of NDR1 Phosphorylated on Ser281 or Thr444

Either 1 microgram GST-NDR1 or HA-NDR1 immunoprecipitated from 100 microgram COS-1 detergent extracts as described above was separated on 10% SDS-PAGE and immunoblotted 2 h at RT or overnight at 4° C. with anti-Ser281P antisera (1:1000) in the presence of 50 microg/ml competing unphosphopeptide or anti-Thr444P purified antibody (1:500). Both antibodies were detected with horseradish peroxidase-conjugated donkey anti-rabbit Ig antibody (Amersham biosciences) and developed by ECL (chemiluminescence; Amersham Pharmacia Biotech).

Western Blotting

To detect GST-NDR1 or HA-NDR1, samples were resolved by 10% SDS-PAGE and transferred to PVDF membranes (Immobilon-P; Millipore). Membranes were blocked in TBST (50 mM Tris-HCl pH 7.5, 150 mM NaCl, and 0.05% Tween-20) containing 5% skimmed milk powder, and were then probed for 2 hours with anti-NDR1_C-term (4 microgram/ml) or 12CA5 monoclonal antibody supernatant (1:100). Bound antibodies were detected with corresponding horseradish peroxidase-linked secondary antibodies and ECL. To detect immunoprecipitated S100B, samples were separated by 18% SDS-PAGE and transferred to PVDF. The membrane was blocked for 2 hours with 5% BSA and 1% FCS in TBST and was then probed with anti-S100B antiserum diluted 1:1000 in the same buffer (TBST with BSA and FCS). Bound antibody was then detected with the corresponding horseradish peroxidase-linked secondary antibody in TBST and ECL.

Coimmunoprecipitation of NDR1 and S100B

Cytoplasmatic COS-1 cell extracts were prepared by lysing the cells for 10 min in a hypotonic buffer: 10 mM HEPES pH7.9, 0.5 mM $CaCl_2$, 1.5 mM $MgCl_2$, 10 mM KCl, 1 mM $Na_3VO_4$, 20 mM beta-glycerolphosphate, 1 microM microcystin-LR, 50 mM NaF, 0.5 mM PMSF, 4 microM leupeptin, 1 mM benzamidine, and 1 tablet/10 ml of Complete protease inhibitors. Afterwards, the cells were homogenised using a Dounce homogeniser. After centrifugation at 3300 g for 15 min, supernatants with cytoplasmic extracts were set aside, and isolated nuclei found in the pellet were further processed by lysis for 30 min in a high-salt buffer: 20 mM HEPES pH 7.9, 25% glycerol, 0.5 mM $CaCl_2$, 1.5 mM $MgCl_2$, 0.5 M KCl, 1 mM $Na_3VO_4$, 20 mM beta-glycerophosphate, 1 microM microcystin-LR, 50 mM NaF, 0.5 mM PMSF, 4 microM leupeptin, 1 mM benzamidine, and 1 tablet/10 ml of Complete protease inhibitors. After centrifugation at 20 000 g for 30 min, the cytoplasmic and nuclear extracts were pooled at a ratio of 4:1. One mg of protein extract was precleared for 60 min with protein A-Sepharose and incubated for 3 h at 4° C. with 5 ml anti-S100B antiserum immobilised on 10 ml protein A-Sepharose. Afterwards, the beads were washed four times in buffer (20 mM HEPES pH 7.9, 25 mM KCl, 5% glycerol, 1 mM $MgCl_2$, 0.1 mM $CaCl_2$, 0.5 mM PMSF, 4 microM leupeptin, 1 mM benzamidine, 1 mM $Na_3VO_4$, 20 mM beta-glycerophosphate, 1 microM microcystin-LR, and 50 mM NaF). Immunoprecipitates were boiled in sample buffer and immunoblotted for S100B or HA-NDR1 as described above.

Mass Spectrometry 10 micrograms of untreated or autophosphorylated GST-NDR1 (2 h at 30° C.; either in the presence or absence of 1 mM $CaCl_2$ and 10 microM bovine S100B homodimer) was separated by 10% SDS-PAGE, stained with Coomassie Blue R-350 (Sigma), and excised from the gel for further processing. Gel slices were sequentially washed 3×8 min in acetonitrile and 2×1 2 min in 25 mM $NH_4HCO_3$. Afterwards, the gel slices were reduced for 1 h at 57° C. in 10 mM DTT followed by alkylation for 45 min at RT in 55 mM iodoacetamide. Upon repeated washing in acetonitrile/$NH_4HCO_3$, gel-bound GST-NDR1 was digested with sequencing grade modified trypsin (Promega) overnight at 37° C. The cleaved peptides were then extracted by two 15 min sonication steps in $H_2O$:acetonitrile:formic acid (20:70:10) and $H_2O$:methanol:formic acid (93:2:5).

All experiments were performed on an API 300 triple-quadrupole mass spectrometer (PE-Sciex, Toronto, Canada) equipped with a NanoESI source (Protana, Odense, Denmark). For precursor ion scans of m/z −79, samples were injected by off-line nano-electrospray according to Wilm and Mann (1996, Anal. Chem. 68, 1-8). The instrument was operated in negative ion mode; a small percentage of ammonia was added in the spraying needle during sample preparation for better sensitivity in the detection of m/z −79. For LC-MS sequence analysis, phosphopeptides were further separated by high performance liquid chromatography (HPLC) interfaced with the API 300 mass spectrometer. The Rheos 4000 chromatograph was equipped with a 1×250 mm Vydac C8 column (Hesperia, Canada). The HPLC column was equilibrated in 95% solvent A (2% $CH_3CN$, 0.05% trifluoroacetic acid in $H_2O$), 5% solvent B (80% $CH_3CN$, 0.045% trifluoroacetic acid in $H_2O$), and a linear gradient was developed from 5 to 50% of solvent B in 60 min at a flow rate of 180 microl/min. After the column, the flow was split with a small percentage (about 5%) being directed to the mass spectrometer. The phosphopeptides were detected in the collected HPLC fractions by Cerenkov counting. For further sequence investigation, phosphopeptides containing fractions were dried, re-dissolved in a few microl of $H_2O$:$CH_3CN$:formic acid (49.5:49.5:1), individually injected into the mass spectrometer using the nano-electrospray source and analysed by low-energy tandem MS experiments in positive ion mode.

Example 1

Mapping of the Ndr1 Autophosphorylation Sites

Both autophosphorylation and Ndr1 kinase activity increase upon incubation of NDR1 with the EF-hand Ca2+-binding S100B protein (Millward et al., 1995; Millward et al., 1998). This Example further analyzes the NDR1 autophosphorylation sites by means of nanospray ESI-MS/MS analysis.

Briefly, 10 microg of GST-NDR1 was left untreated or was autophosphorylated for 2 hours in the absence or presence of 1 mM $CaCl_2$ and 10 mM bovine S100B. After separation by SDS-PAGE, GST-NDR1 was excised and processed by tryptic cleavage for mass spectrometry analysis of phosphopeptides. The resultant mixtures of tryptic peptides were introduced into a triple-quadrupole mass spectrometer and analysed for phosphorylated peptides by precursor ion scanning for m/z −79 in negative ion mode. This procedure detects each peptide in the mixture that, upon fragmentation in the collision cell, liberates a species of m/z −79, representing a negative fragment ion $PO^{3-}$ characteristic of phosphorylated peptides (Carr et al., 1996, Anal. Biochem. 239, 180-192; Wilm et al, 1996, Anal. Chem. 68, 527-533). Phosphopeptides whose m/z could be assigned to NDR1-derived phosphopeptides were labeled P1 through P4 for convenience. Some of the peptides (e.g., P2 and P1) were detected in multiple charged states. Peptide P2 results presumably from trace chymotryptic contamination of the trypsin preparation since it overlaps with P1 and terminates with an aromatic residue. An abundant, double-charged nonphosphorylated NDR1 peptide (aa 378-391 of SEQ ID NO:2) was detected with a m/z 860.

The phosphopeptides, P1-P4 (amino acids 277-301, 277-294, 438-447 and 72-78 of SEQ ID NO:2, respectively), which derive from three regions of the NDR1 polypeptide are summarised with the phosphoacceptor residues marked by number referring to Ndr 1 full length sequence.

| Peptide | Sequence | Predicted mass (Da) | Detected mass (Da) | Difference (Da) |
|---|---|---|---|---|
| P1 | QLAFS$^{281}$TVGTPDYLAPEVFMQTGYNK | 2778.1 | 2858.8 (+/−1.1) | +80.7 |
| P2 | QLAFS$^{281}$TVGTPDYLAPEVF | 1955.2 | 2034.6 (+/−0.7) | +79.4 |
| P3 | DWFINYT$^{444}$YKR | 1504.7 | 1585.8 | +81.1 |
| P4 | KET$^{74}$EFLR | 922.0 | 1001.8 | +79.8 |

When non-treated GST-NDR1 was analysed by precursor ion scan of m/z −79, only weak phosphopeptide signals corresponding to peptides P2 and P4 could been detected. With the GST-NDR1 samples autophosphorylated either in the absence or presence of Ca2+/S100B, however, the abundance of phosphorylated peptides markedly increased. The observed m/z value of most of these signals could be assigned in both samples to four NDR1-derived phosphopeptides P1-P4 which, upon liberation of the phosphate group (79.97 Da), gave rise to expected tryptic (or in one case chymotryptic) NDR1 dephosphopeptides.

To confirm the identity of these peptides, an LC-MS analysis of GST-NDR1 autophosphorylated with [gamma-$^{32}$P] ATP was performed. After collection of the phosphopeptide-enriched radioactive fractions, the samples were analyzed by ESI mass spectrometry using m/z −79 precursor ion scanning method. The same species as in the analysis of the unlabelled GST-NDR1 was found and a low-energy tandem mass spectrometry (MS/MS) analysis was then performed in positive ion mode. Ion species corresponding to phosphopeptides listed above were detected, including the phoshorylated residues, thereby confirming the identity of NDR1 in vitro autophosphorylation sites.

The four phosphopeptides derive from three regions of the NDR1 polypeptide. The first three phosphopeptides correspond to sites previously identified in NDR1 activated in vivo by okadaic acid. P1 and P2 assign to phosphopeptides encompassing Ser281 of the activation segment and P3 represents a phosphopeptide containing the residue Thr444 from the hydrophobic motif located in the carboxyl-terminal region of NDR1 (see EP1097989, entitled "Ndr phosphokinase"). The phosphopeptide P4 comprises a previously unidentified phosphoresidue, Thr74, from the N-terminal region of NDR1 defined as the S100-binding region encompassing aa62-83 (Millward et al., 1998).

Thus, this Example shows that NDR1 autophosphorylates on three residues in vitro. The first of them, Thr74 is located in the N-terminal S100B-binding domain of NDR1. The second, major site Ser281, which is well conserved among all AGC group kinases, constitutes an essential part of activation segment (also known as "T-loop") in the subdomain VIII of the kinase catalytic domain, immediately after the nuclear localisation signal and kinase domain insert of NDR1. The third site, Thr444, also conserved in the AGC superfamily, is located outside of the kinase catalytic domain in a region enriched with hydrophobic amino acid residues (therefore referred to as the "hydrophobic motif").

Example 2

Reduction of Autophosphorylation Rate and Kinase Activity in GST-Phosphorylation-Site Mutants To confirm the in vitro autophosphorylation of NDR1 on the residues Thr74, Ser281, and Thr444, and to estimate the influence of these residues on the autophosphorylation-induced kinase activity of NDR1, a series of GST-NDR1 mutants were constructed replacing the phosphorylation site residue with an alanine, or Lys 118 in the catalytic site with an alanine to form a GST-NDR1 kinase-dead mutant. These were assayed for autophosphorylation and kinase activity.

In brief, 1 microgram of purified GST-NDR1 (in solution ~0.5 microM) wild type, kinase dead (K118A), and alanine mutants of phosphorylation residues Thr74, Ser281, and Thr444 were autophosphorylated for 2 hours in vitro without further additions or in the presence of 1 mM $CaCl_2$ and 10 microM bovine S100B. Proteins were visualized on SDS gels using Coomassie Blue R-350 stained SDS-PAGE gel, and [gamma-$^{32}$P]ATP-labelled proteins were visualized by autoradiography of the gels developed on a Phosphorimager screen. The amount of incorporated $^{32}$P was quantified by Cerenkov counting.

|       | WT     | K118A  | T74A   | S281A  | T444A  |
|-------|--------|--------|--------|--------|--------|
| −S100B| 0.1688 | 0.0076 | 0.158  | 0.0192 | 0.1232 |
| +S100B| 0.3512 | 0.0064 | 0.2072 | 0.028  | 0.2412 |
| SD1   | 0.0244 | 0.0032 | 0.0304 | 0.012  | 0.0176 |
| SD2   | 0.0332 | 0.0028 | 0.0164 | 0.0032 | 0.0112 |

Specific activity of GST-NDR1 mutants was also measured by a peptide kinase assay as described above. For this purpose, 1 microgram of purified GST-NDR1 wild type and alanine mutants were left without further treatment or autophosphorylated for 2 h in the presence or absence of 1 mM $CaCl_2$ and 10 mM bovine S100B.

|       | WT     | K118A  | T74A   | S281A  | T444A  |
|-------|--------|--------|--------|--------|--------|
| CTRL  | 1      | 0.158  | 1.006  | 0.16   | 0.564  |
| −S100B| 4.106  | 0.272  | 3.786  | 0.514  | 1.92   |
| +S100B| 21.348 | 0.222  | 7.818  | 0.952  | 3.974  |
| SD1   | 0.052  | 0.062  | 0.162  | 0.078  | 0.144  |
| SD2   | 0.36   | 0.092  | 0.172  | 0.18   | 0.082  |
| SD3   | 0.926  | 0.124  | 0.552  | 0.108  | 0.412  |

Wild-type GST-NDR1 became efficiently autophosphorylated in vitro (up to 0.4 pmol ATP/pmol GST-NDR1), whereby addition of S100B homodimers brought about an approximate 2-fold increase in autophosphorylation (on both Ser281 and Thr444) accompanied by about a 5-fold increase in kinase activity. Since the kinase-dead mutant did not show detectable autophosphorylation, the NDR1 kinase activity is thought to account for the observed effects. The S281A mutant displayed a dramatically reduced autophosphorylation rate (irrespective of addition of S100B), thereby confirming that this residue is the major in vitro autophosphorylation site of NDR1. The kinase activity of S281A decreased similarly, being almost undetectable.

The T444A point mutation also led to a significant decrease of both autophosphorylation rate and kinase activity (about 5-fold), although not to the same extent as S281A, indicating that T444 is also susceptible to autophosphorylation in vitro. Although not wishing to be bound by theory, the less marked effects of T444A, as compared to the S281A mutation, may be readily explained by the unfavorable, hydrophobic peptide sequence upstream of this residue with only two remote basic amino acids.

Finally, the T74A mutant displayed only a negligible reduction in autophosphorylation rate and kinase activity in the absence of Ca2+/S100B. According to quantitative analyses by LC-MS, the phosphorylation at this site accounted for less than 5% of the total phosphate incorporation. After addition of Ca2+/S100B, however, the impact of this point mutation approached that of T444A, and the stimulatory effect of Ca2+/S100B on autophosphorylation rate and kinase activity was strongly diminished as compared to the other GST-NDR1 variants. These results indicate that Thr74 represents only a minor autophosphorylation site, and the low responsiveness to the addition of Ca2+/S100B most likely reflects the inability of the T74A mutant to interact with S100B.

Thus, the mutational analysis shows that the Ser81 residue of Ndr1 is responsible for the major part of phosphate incorporation into autophosphorylated NDR1, whereas Thr74 and Thr444 account for a minor fraction of the incorporated phosphate. Moreover, mutation of Ser281 led to a dramatic decrease of NDR1 autophosphorylation-induced kinase activity thereby confirming this residue as the major NDR1 autophosphorylation site. However, the results imply that both Ser281 and Thr444 are necessary for the fully active NDR1 and point to a synergy between these two residues in the activation of NDR1.

Example 3

Ca2+/S100B Promote the Autophosphorylation of GST-NDR1 on Both Ser281 and Thr444 Through Thr74 Phosphorylation To reliably quantify the effect of S100B on NDR1 phosphorylation status, rabbit polyclonal antibodies were raised against phosphoepitopes comprising Ser281 or Thr444. GST-NDR1 mutants were treated essentially as described in Example 2 and detected either with anti-NDR1_C-term antiserum or polyclonal antibodies recognising NDR1 phosphorylated on Ser281 or Thr444. These antibodies possessed an exclusive specificity for the phosphorylated NDR1 since corresponding phosphorylation point mutants S281A or T444A or kinase-dead were not recognised.

Using these reagents, Ca2+/S100B was found to enhance phosphorylation on both Ser281 and Thr444 (similarly to the general increase in autophosphorylation seen in Example 2) without an apparent preference for either residue. Whereas the S281A mutation entirely abolishes the autophosphorylation on Thr444, the T444A mutant displayed an almost normal autophosphorylation on Ser281. Although Thr444 is only autophosphorylated to a minor extent, these data indicate that the impact of the activation segment phosphoresidue on the NDR1 kinase activity is higher than the impact of the hydrophobic motif residue, or that these residues are phosphorylated in a sequential manner as it is known for most of other AGC family protein kinases (Newton, A. C. (2001) Chem. Rev. 101, 2353-2364). Finally, the T74A point mutation abolished the S100B-mediated increase of phosphorylation for both Ser281 and Thr444 residues without affecting the intrinsic NDR1 autophosphorylation, again stressing the crucial role of this residue in interaction with S100B.

Example 4

Ser281 is the Major Autophosphorylation Residue Whereas Thr444 is Targeted by an Upstream Kinase In Vivo To evaluate the relative influence of the individual phosphorylation sites on kinase activity of NDR1 in vivo, we constructed a series of mammalian expression vectors with HA-tagged NDR1 wild type, kinase dead, and alanine mutants in the three identified phosphorylation sites.

COS-1 cells expressing either wild type HA-NDR1 or the indicated mutants were treated for 1 h with 1 microM okadaic acid or with solvent alone. HA-tagged NDR kinase variants were then immunoprecipitated (out of 100 microgram of detergent extracts) with 12CA5 monoclonal antibody and assayed for kinase activity by a peptide kinase assay as described above.

|     | WT      | K118A  | T74A   | S281A  | T444A  |
|-----|---------|--------|--------|--------|--------|
| −OA | 0.3532  | 0.0107 | 0.124  | 0.0357 | 0.1067 |
| +OA | 10.8852 | 0.0204 | 1.053  | 0.1113 | 0.6019 |
| SD1 | 0.0499  | 0.005  | 0.0149 | 0.0013 | 0.0232 |
| SD2 | 1.6629  | 0.0131 | 0.1455 | 0.0177 | 0.1361 |

Point-mutations in the two established in vivo regulatory phosphorylation sites, Ser281 and Thr444, led to an expected decline of NDR1 kinase activity in both untreated and 1 microM okadaic acid-treated COS-1 cells (again with some preference for the S281A mutant). In contrast to the GST-NDR1 kinase assays, however, a drastic reduction of HA-NDR1 kinase activity was detected after mutating Thr74. This indicates that the Thr74-dependent, S100B-mediated autophosphorylation may play a crucial role in vivo.

To examine this possibility, extracts from transfected COS-1 cells were analyzed with the anti-Ser281P and anti-Thr444P antisera. Protein extracts (10 microg) from transfected COS-1 cells were immunoblotted with 12CA5 to verify similar expression levels of each HA-NDR1 construct. For the analysis of phosphorylation status, 12CA5-immunoprecipitated HA-NDR1 variants (out of 100 microg protein extract) were analysed by immunoblotting with phosphospecific antibodies directed against P-S281 or P-T444.

The Ser281 residue was constitutively phosphorylated in vivo (and this phosphorylation was further enhanced after treatment with 1 mM okadaic acid) whereas the Thr444 site only became phosphorylated after okadaic acid treatment. The phosphorylation of Ser281 entirely depends on the activity of NDR1 since the kinase-dead K118A mutant did not display any phophorylation on this position. This fact implies that Ser281 is an autophosphorylation residue also in vivo. This was confirmed by orthophosphate metabolic in vivo labeling. Mutation of Thr444, however, did not impair phosphorylation of Ser281, which again points to the low importance of this residue for NDR1 autophosphorylation. The Thr444 residue, however, became phosphorylated even after abolishing the kinase activity of NDR1 in the kinase-dead mutant K118A, implicating it as a target of an upstream kinase. Finally, the mutation of the residue Thr74 led to a marked reduction of both Ser281 and Thr444 phosphorylation (both with and without okadaic acid treatment), in agreement with the kinase activity data. This implicates Thr74 not only in the S100B-mediated autophosphorylation of NDR1, but also in targeting the upstream kinase to NDR1.

Example 5

Phosphorylation on Both Ser281 and Thr444 Occurs in a Ca2+-Dependent Manner

Since Ca2+/S100B is essential both for NDR1 activity in vivo and for an efficient NDR1 autophosphorylation on Ser281 and Thr444 in vitro, and since the S100B-NDR1 interaction is known to be fully Ca2+ dependent (Millward et al., 1998), this Example investigates the role of intracellular Ca2+ in the activation of NDR1, i.e. in phosphorylation of NDR1 on Ser281 or Thr444 or both. For this purpose, COS-1 cells were trasfected with the membrane-permeable agent BAPTA-AM which is freely taken up into cells, where it is hydrolysed by cytosolic esterases and trapped intracellularly as an active, membrane-impermeable Ca2+ chelator BAPTA (Taylor and Broad, 1998, Trends Pharmacol. Sci. 19, 370-375).

Mock-transfected or HA-NDR1-expressing COS-1 cells were treated for 1 h with 1 mM OA, 50 microM BAPTA-AM, and 20 mM thapsigargin or with solvent (0.1% DMF or 0.1% DMSO) alone. 12CA5 immunoprecipitates (out of 100 microgram protein extract) were then assayed using the peptide kinase assay for NDR1 kinase activity.

|                | −O−<br>B−T | +O−<br>B−T | −O+<br>B−T | +O+<br>B−T | +O+<br>B+T |
|----------------|---------|---------|---------|---------|---------|
| Spec. Activity | 0.5738  | 10.142  | 0.2676  | 1.14503 | 7.43613 |
| SD             | 0.06203 | 1.21575 | 0.0328  | 0.14243 | 0.89176 |

Protein extracts (10 microg) from mock- and HA-NDR1-transfected COS-1 cells were also immunoblotted with 12CA5 to verify equal expression levels of HA-NDR1 construct. For the analysis of phosphorylation status, 12CA5-immunoprecipitated HA-NDR1 (out of 100 microgram protein extract) was analysed by immunoblotting with phosphospecific antibodies directed against P-S281 or P-T444.

50 mM BAPTA-AM dramatically reduced the okadaic acid-stimulated NDR1 activity almost to basal activity level of the okadaic acid-nonstimulated cells. Likewise, examination of phosphorylation status of NDR1 demonstrated that phosphorylation on both Ser281 and Thr444 declined almost to the baseline. Notably, both NDR1 activity and the phosphorylation of Ser281 and Thr444 were rescued by coincubation of BAPTA-AM with 20 mM thapsigargin, a sesquiterpene lactone raising cytoplasmatic Ca2+ by inhibition of the sarcoplasmatic-endoplasmatic reticulum $Ca^{2+}$ ATPase (SERCA) pumps, i.e. through liberation of intracellular $Ca^{2+}$ stores (Treiman et al., 1998, Trends Pharmacol. Sci. 19, 131-135). These results confirm $Ca^{2+}$ specificity of the observed BAPTA-AM effects and combined with the data above show that NDR1 is regulated by Ca2+-dependent, most likely S100B-mediated autophosphorylation on Ser281 and by phosphorylation by an as yet unidentified Ca2+-dependent upstream kinase on Thr444.

In summary, both autophosphorylation of NDR1 on Ser281 as well as phosphorylation by an upstream kinase on Thr444 are Ca2+-dependent processes. Upon addition of Ca2+/S100B, an increased phosphorylation on Ser281 and Thr444 was observed, which resulted in the stimulation of NDR activity. The Ca2+-chelating agent BAPTA-AM suppressed activity and phosphorylation of NDR1 on both Ser281 and Thr444, and specifically, these effects were reversed upon addition of the SERCA Ca2+-pump inhibitor thapsigargin. Although not wishing to be bound by theory, the Ca2+ dependence of autophosphorylation of NDR1 on Ser281 can be readily explained by requirement of NDR1 for Ca2+/S100B to autophosphorylate efficiently.

Example 6

Thr74 is Required for the Association of HA-NDR1 with Ca2+/S100B

NDR1 forms functional complexes with S100B in vivo depending on an intact N-terminal domain of NDR1 (Millward et al., 1998). This Example demonstrates that the association depends on the phosphorylation status of NDR1. COS-1 cells were transfected with S100B and NDR1 wild type or alanine mutant expression plasmids, and the NDR1-S100B interaction was monitored by coimmunoprecipitation of NDR1 with S100B.

COS-1 cells were transfected with HA-NDR1 wild type, kinase dead (K118A), and alanine mutants of phosphorylation residues Thr74, Ser281, or Thr444, and S100B or corresponding empty vectors as indicated. Forty-eight hours later, non-detergent nuclear and cytoplasmatic cell lysates were prepared, pooled and analysed for expression of HA-NDR1 variants. 1 mg of protein extracts were further immunoprecipitated with anti-S100B-Sepharose and analysed for S100B expression and association of NDR1 with anti-S100B immunoprecipitates.

The formation of NDR1-S100B complexes is independent of NDR1 kinase activity or phosphorylation status of the regulatory residues Ser281 and Thr444, and thus, appears to be constitutive. However, Thr74 (the minor in vitro autophosphorylation site) seems to be essential for NDR1 to undergo the interaction with Ca2+/S100B. The N-terminal domain of NDR1 seems to exert an autoinhibitory effect on the kinase catalytic domain that can be relieved by binding of S100B or other potential interacting proteins.

Example 7

Molecular Characterization of NDR2 Protein Kinase

This Example describes the identification and molecular characterization of NDR2 protein kinase. NDR1 and NDR2 are isoforms sharing an 86% amino acid identity and are highly conserved between human and mouse. The data shows that NDR2 is potently activated by okadaic acid treatment, which results in the phosphorylation on Ser-282 and Thr-442. NDR2 is also shown to be regulated by EF-hand calcium-binding S100B proteins. In vitro, S100B induces autophosphorylation of NDR protein kinase on Ser 282 and T442.

BLAST searches of the NCBI database identified the human KIAA0965 mRNA (Genebank accession number AB023182 clone hj06174s1) to be a partial cDNA with significant homologies to human NDR1 protein kinase. The complete cDNA was isolated by PCR screening in a Marathon-Ready human brain cDNA library (Clontech) following standard protocols (www.clontech.com, PT1156-1). The mouse Ndr1 cDNA was cloned by screening several mouse cDNA libraries in λZAPII (Stratagene), the mouse Ndr2 cDNA with the 3' mEST (genebank accession number AA277870 and subcloning the 5' end from mouse brain library (Clontech) by a touchdown approach following standard protocols (www.clontech.com, PT 1156-2). All clones were fully sequenced on both strands using Sequenase (United Sates Biochemical) and custom synthesized primers and compared with a genomic database (Ensembl).

Mammalian expression vectors encoding HA-epitope tagged hNdr1 are described in Example 1. Expression vectors for HA-hNdr2 were constructed by amplifying the respective untagged cDNAs with primers 5'-CTTCCAAGCTTAGTC-GACATGGCTTACCCATACGATG TTCCAGA-3' (SEQ ID NO:23) and 5'-TTACGCTTCGGCAATGACGGCAGG-GACTACAACA ACC-3' (SEQ ID NO:24) and 5'-GGATC-CTCTAGAGGTTATGGGTGAATGTTAT-CTTCAT AACT-TCC-3' (SEQ ID NO:25) using Pfu Polymerase (Promega), the PCR product was then cut with HindIII and XbaI and cloned into pCMV5. GST-Ndr2 and GFP-Ndr2 were constructed by amplifying the Ndr2 cDNA with primers 5'-CGG-GATCCGGTACCAT-GGCAATGACGGCAGGGACTAC-3' (SEQ ID NO:26) and 5'-CGGGATCCCTTCATTCATA ACTTCCCAGC-3' (SEQ ID NO:27) using Pfu polymerase (Promega). The PCR product was then cut with BamHI and cloned into pGEX2T (Smith, D. B. and Johnson, K. S. (1988) Single-step purification of polypeptides expressed in *Escherichia coli* as fusions with glutathione S-transferase Gene 67 (1), 31-40) and pEGFP-C1 (Clontech). The direction of the insert was then checked by KpnI digest and sequencing. GFP-Ndr1 was constructed by amplifying the Ndr1 cDNA with primers 5'-AGCAGGATCCGGTACCATGGCAA-TGACAGGCTCAACACCT TGC-3' (SEQ ID NO:28) and 5'-CGAGGATCCTGCTCCACATAGGATTC-CGTG-GCAAGAG-3' (SEQ ID NO:29) and cloned into pEGFP-C1 (Clontech) and checked by sequencing. GFP-Ndr2 was constructed in essentially the same manner.

All other procedures (including bacterial expression, kinase assays, immunodetection and mass spectrometry) were carried out essentially as described in the Methodology section above.

To examine the NDR kinase subfamily the sequences of hNdr2, mNdr1 and mNdr2 cDNAs and gene sequences were determined. The deduced amino acid sequences were compared and aligned to the known sequences of hNDR1, *D. melanogaster* NDR TRC, *C. elegans* NDR Sax-1 and *S. cerevisiae* CBK1. The human and mouse NDR1 sequence show an identity of 99%, the NDR2 sequences are 97% identical, whereas NDR1 and NDR2 show an identity of 86%. Human Ndr2 exhibits a high degree of conservation through evolution with 68%, 67% and 47% identity with Drosophila, *C. elegans* and yeast, respectively. Human and mouse NDR2 are 464 amino acids in length, with a predicted mass of 54.0 kDa. Gene mapping indicates that hNdr1 and mNdr1 as well as hNdr2 and mNdr2 are located on orthologous regions. hNdr1 is mapped to 6p21 (Tripodis N. et al.), hNdr2 to 12p12.3, whereas the corresponding mouse genes are mapped to 17B1 and 6G2-G3. Additionally pseudogenes of Ndr2 were found on chromosome 1 D and 8A1.2 of the mouse genome. The intron-exon boundaries are conserved within all human and mouse genes. The human and mouse genes comprise 14 exons with conserved intron-exon boundaries. Exon 1 is a non coding exon containing a 5' UTR; exon 2 contains the start codon; and the stop codon is located in exon 14.

Comparision of the sequence of NDR2 with NDR1 shows that NDR2 contains Ser-282 and Thr-442 corresponding to the NDR1 phosphorylation sites Ser-281 and Thr-444 (Millward et al.), suggesting that NDR2 activity is regulated in the same way as NDR1. To further examine this NDR2 mutants were created in which either Ser-282 or Thr-442 were replaced by an alanine. Additionally an in vitro phosphorylation site mutant T75A essentially as described above, and a kinase dead mutant K119A was created for Ndr2. The protein kinase activity of each of these mutants was measured following cell treatment with okadaic acid (OA) or solvent alone. HA-NDR2-WT was potently stimulated (~10-fold) by OA. All the phosphorylation site mutants (S282A, T442A and T75A) had a markedly reduced basal activity but were still activated. The K119A mutant reduced basal activity to nearly undetectable levels, and didn't show any activation by OA.

Western blot analysis of the regulatory phosphorylation site mutants S282A and T442A with phosphorylation site specific antibodies developed against Ser281 and Thr442 of NDR1 shows that NDR becomes phosphorylated on Ser282 in NDR2 wt, as well as in the T442A and T75A mutants, and that this phosphorylation is increased after OA treatment in NDR2 wt and T442A, but not in T75A. The kinase dead K119A mutant is not phosphorylated on S282. T442 becomes phosphorylated upon OA treatment in NDR2 wt (wild type), as well as the S282A, the T75A and the K119A mutants. This was described above for the corresponding mutants of NDR1. Western blot analysis confirmed that wt and mutants were expressed at comparable levels. These results confirm that phosphorylation on both the activation loop phosphorylation site 282 and the regulatory hydrophobic motif phosphorylation site T442 are required for NDR2 activation.

The sequence conservation between NDR1 and NDR2 also encompasses the previously defined S100 binding domain of NDR1. Therefore, the in vitro effect of Ca2+/S100B on NDR2 activity was measured in a time and concentration dependent manner. Ca2+/S100B increases the rate of NDR2 autophosphorylation by ~2-fold after 4 hours of incubation, as measured by mass spectrometry anlaysis, and it stimulates the specific NDR activity in a concentration dependent manner up to ~4-fold. This suggests that NDR2 is activated by Ca2+/S100B in the same way as NDR1. After in vitro incubation of GST-NDR2 in the presence and absence of Ca2+/S100B, the proteins were digested with trypsin, and the resultant mixture was analysed by ESI-MS-MS in a −79 precursor scan, measuring the mass charge ratio (m/z) of all peptide species that liberate a single phosphate group after fragmentation. The identity of 5 NDR2 derived phosphopeptides could be determined in both samples, the GST-NDR2 and the GST-NDR2/Ca2+/S100B.

| Detected Phosphopeptides | m/z (amu) | NDR2 a.a (SEQ ID NO: 4) |
| --- | --- | --- |
| [M-2H]2-<br>QLAYSTVGTPDYIAPEVF | 1024 | 277-294 |
| [M-3H]3-<br>QLAYSTVGTPDYIAPEVFMQTGYNK | 957 | 277-301 |
| [M-3H]3-<br>QLAYSTVGTPDYIAPEVF | 683 | 277-294 |
| [M-2H]2-<br>DWVFLNYTYKR | 791 | 434-444 |
| [M-2H]2-<br>RKTEFL | 500 | 73-78 |

Three of these peptides are derived from a region corresponding to the activation (or T-loop of NDR2) containing the Ser-282 phosphorylation site. A fourth phosphopeptide comes from the carboxyterminal region of the NDR2 polypeptide containing the regulatory phosphorylation site Thr-442, a fifth one corresponds to Thr-75, a site within the S100B binding domain. These results demonstrate that NDR2 is regulated by S100B proteins in the same way as NDR1.

Example 8

Human Ndr Interacts with hMOB1 (GI: 11691898)

HA-tagged hNDR and myc-tagged hMOB1 were cotransfected in COS1 cells, which were stimulated with okadaic acid or solvent alone. After cell lysis and extract preparation, HA-NDR was immunoprecipitated and co-immunoprecipitated myc-hMOB1 detected or Myc-hMOB1 was immunoprecipitated and co-immunoprecipitated HA-NDR detected. Co-immunoprecipitation of myc-hMOB1 with HA-NDR1, as well as co-immunoprecipitation of HA-NDR with myc-hMOB1 revealed that MOB1 can associate with NDR1 and that this interaction is dependent on stimulation of the cells with OA.

Because of this dependence of the interaction on stimulation by the PP2A-inhibitor and NDR activator OA, we tested if the interaction depends on NDR kinase activity. HA-NDR, wt and mutants, and myc-hMOB1 were cotransfected into COS-1 cells and the cells were treated with OA prior to lysis. HA-NDR was immunoprecipitated and the coimmunoprecipitated myc-hMOB1 detected. The kinase dead mutant with a mutated catalytic lysine in the ATP binding site, K118A, is still able to interact with hMOB1 after okadaic acid stimulation. Furthermore, the two important in vivo phosphorylation sites of NDR, serine-281 in the activation segment and the hydrophobic motif site threonine-444 in the C-terminal regulatory domain were tested, as well as the threonine 74 site in the N-terminal regulatory domain, for their role in NDR-MOB interaction. The mutants S281A and T444A still interact with MOB1 after OA stimulation, while the T74A mutant shows a complete absence of interaction with MOB1.

To test if endogenous NDR interacts with hMOB1, myc-hMOB1 was transfected into COS1 cells and treated 16 h after transfection prior to lysis with OA or solvent alone. Myc-hMOB1 was then immunoprecipitated with 9E10 antibody (Evan et al, Isolation of monoclonal antibodies specific for human c-myc proto-oncogene product. Mol. Cell. Biol. 5:3610-3616, 1985) coupled to protein G Sepharose or, as control, protein G Sepharose beads alone. Co-immunoprecipitated endogenous NDR was then detected with a monoclonal anti-NDR antibody. Endogenous NDR was found to interact with myc-mob in an OA stimulation dependent manner.

Taken together, these results show that NDR interacts with hMOB1 in an okadaic acid stimulation, but not kinase activity, dependent manner and that the residue T74 in the N-terminal regulatory domain of NDR plays an important role in this interaction.

Example 9 hMOB1 Stimulates NDR Kinase Activity

To test whether hMOB1 plays a role in NDR activation, myc-hMOB1 or the empty vector was cotransfected with HA-NDR1 in COS1 cells and treated with OA. 12CA5 immunoprecipitates were then assayed using the peptide kinase assay for HA-NDR kinase activity. The results revealed a two to threefold stimulation of OA stimulated NDR kinase activity, indicating a role for hMOB1 in NDR activation. GST-MOB and GST respectively was added to immunoprecipitated HA-NDR and kinase reaction were performed. The reactions were resolved on a 10% SDS PAGE and the radioactivity visualised by using a phosphoimager. Addition of GST-hMOB1 to HA-NDR kinase reactions stimulated NDR autophosphorylation activity.

Example 10

The N-Terminal Domain of NDR is Important for Kinase Activation

This Example illustrates the importance of the N-terminal domain in kinase activation. Point mutations of highly conserved residues in the N-terminal to alanine induced strong inhibition of OA stimulated kinase activity. The mutation of arginine 41, arginine 44 or leucin 48 to alanine, all of which lie in a predicted first alpha-helix spanning amino acids 40 to 55, and are situated close together on the same side of the alpha-helix, reduces kinase activity to below 20% of the wild type activity. Residues in a predicted second alpha-helix, situated in the S100B binding region of NDR, spanning amino acids 60 to 80, also leads to inhibition of kinase activity. Mutation of lysine 72, glutamate 73, threonine 74, arginine 78 or leucine 79 to alanine reduces kinase activity to 20% or lower. The first part of the N-terminal domain, spanning amino acids 1 to 33 and containing a predicted beta-sheet in hNDR, was also revealed to be important for kinase activation. Deletion of the first 30 amino acids completely abolished kinase activation. Point mutations in this region strongly reduced kinase activity as well, with a mutation of threonine 16, glutamate 18 and glutamate 28 resulting in a kinase activity of about 40% of wt, and mutation of lysine 24 and tyrosine 31 resulting in a kinase activity of about 20% of wild-type. These results implicate an important role for the highly conserved residues of the NDR-family activation domain (NFAD) in kinase function.

Example 11

The NDR Family Activating Domain, NFAD, is Required for NDR-MOB Interaction

This Example demonstrates that T74 is not only important for NDR kinase activity and interaction with S100B, but is also required for NDR-mob interaction. HA-NDR N-terminal point mutants and myc-mob1 were co-transfected into COS1 cells which were treated with OA prior to lysis. HA-NDR mutants were immunoprecipitated and coimmunoprecipitated myc-hMOB1 detected. Cotransfection of HA-tagged NDR mutants and myc-hMOB1 and subsequent co-immunoprecipitation of myc-MOB with HA-NDR revealed that several of the conserved residues, which are important for kinase activation are required for NDR-MOB interaction as well. Replacement of tyrosine 31, arginine 41, threonine 74 or arginine 78 with alanine was not tolerated for the interaction with MOB under the conditions tested, while the lysine 24, arginine 44 and leucine 79 mutants showed a reduced interaction. Only three of the mutants that have a strongly reduced kinase activity have no reduction in MOB binding ability: arginine 48, lysine 72 and glutamate 73. Taken together, the results show that the NFAD is important for NDR-hMOB1 interaction.

Example 12

NDR-hMOB1 Interaction Depends on Okadaic Induced Modification on MOB1, While Okadaic Acid Induced Phosphorylation on NDR is Not Required This Example addresses the question as to whether the OA dependence of the NDR-hMOB1 interaction is dependent on an OA-induced modification of NDR or hMOB1 (or by OA treatment of the cells). COS-1 cells were transfected with HA-NDR and myc-hMOB1 separately and stimulated with OA or left unstimulated prior to lysis. The lysates (HA-NDR– or + OA with myc-hMOB1– or + OA) were then pooled, immunoprecipitated with an anti-HA antibody, and myc-mob1 detected. In the two combinations containing myc-MOB of OA treated cells, myc-MOB strongly associated with HA-NDR, regardless of whether the HA-NDR was from OA treated cells or from unstimulated cells. Myc-mob of unstimulated cells showed only a weak interaction with HA-NDR of unstimulated as well as of OA stimulated cells. Therefore, we can conclude that OA induced modification of NDR is not required for the interaction with mob, while hMOB1 OA-dependent modification is needed.

Example 13

The $Ca^{2+}$ Chelator BAPTA-AM Reduces NDR-MOB Interaction

Treatment of COS1 cells with the $Ca^{2+}$ chelator BAPTA-AM reduces OA induced NDR kinase activation. In this Example, the effect of treatment of COS1 cells with BAPTA-AM on the NDR-MOB Interaction was determined. HA-NDR and myc-MOB1 was cotransfected into COS1 cells and the cells were treated with BAPTA-AM and OA or the solvents alone prior to lysis. HA-NDR was immunoprecipitated and co-immunoprecipitated myc-MOB1 detected. The kinase activity of the HA-NDR immunoprecipitates was measured in a peptide kinase assay. Co-immunoprecipitation of myc hMOB1 with HA-NDR of BAPTA and OA treated cells revealed a BAPTA-AM induced reduction of the NDR-MOB interaction corresponding to the observed reduction of the NDR kinase activation.

The invention claimed is:

1. An isolated antibody that specifically binds to a polypeptide, wherein the polypeptide is nuclear, Dbf-2 related (Ndr) phosphokinase having the amino acid sequence of SEQ ID NO:2, wherein the polypeptide is phosphorylated at amino acid Thr-74, or the polypeptide has the amino acid Thr-74 replaced by an acidic amino acid residue; and wherein the antibody recognizes an epitope comprising the phosphorylated amino acid, the epitope comprising a S100 binding region encompassing amino acids 62-83.

2. The isolated antibody of claim 1, wherein the antibody is monoclonal.

* * * * *